(12) United States Patent
Hershoff

(10) Patent No.: US 9,788,997 B2
(45) Date of Patent: Oct. 17, 2017

(54) EYE CONTACT LENS INSERTION AND REMOVAL APPARATUS

(71) Applicant: Craig L. Hershoff, Sunny Isles Beach, FL (US)

(72) Inventor: Craig L. Hershoff, Sunny Isles Beach, FL (US)

( * ) Notice: Subject to any disclaimer, the term of this patent is extended or adjusted under 35 U.S.C. 154(b) by 0 days.

(21) Appl. No.: 14/661,230

(22) Filed: Mar. 18, 2015

(65) Prior Publication Data

US 2015/0265467 A1    Sep. 24, 2015

Related U.S. Application Data

(60) Provisional application No. 61/955,409, filed on Mar. 19, 2014.

(51) Int. Cl.
*A61F 9/00* (2006.01)

(52) U.S. Cl.
CPC .... *A61F 9/0061* (2013.01); *A61F 2009/0035* (2013.01)

(58) Field of Classification Search
USPC .............................. 294/1.2; 606/107; 206/5.1
See application file for complete search history.

(56) References Cited

U.S. PATENT DOCUMENTS

| 3,139,298 A | 6/1964 | Grabiel | |
|---|---|---|---|
| 3,304,113 A * | 2/1967 | Hutchison | A61F 9/0061 294/1.2 |
| 3,424,486 A * | 1/1969 | Corley | A61F 9/0061 294/1.2 |
| 3,600,028 A | 8/1971 | Henning | |
| 3,697,109 A | 10/1972 | Parrent | |
| 3,743,337 A | 7/1973 | Crary | |
| 3,791,689 A | 2/1974 | Boone et al. | |
| 3,879,076 A | 4/1975 | Barnett | |
| 3,897,968 A * | 8/1975 | Allen, Jr. | A61F 9/0061 294/1.2 |
| 4,082,339 A | 4/1978 | Ross | |
| 4,093,291 A | 6/1978 | Schurgin | |
| 4,113,297 A | 9/1978 | Quinn | |
| 4,123,098 A * | 10/1978 | Shoup | A61F 9/0061 294/1.2 |
| 4,193,622 A | 3/1980 | Overman | |

(Continued)

FOREIGN PATENT DOCUMENTS

| DE | 3315183 | 11/1983 |
|---|---|---|
| EP | 0079869 | 1/1984 |
| GB | 2337699 | 12/1999 |

*Primary Examiner* — Paul T Chin
(74) *Attorney, Agent, or Firm* — Saliwanchik, Lloyd & Eisenschenk

(57) ABSTRACT

Contact lenses are a commonly used medical device that many users find difficult to insert and remove from the eyes. A contact lens insertion and removal apparatus of the subject invention utilizes a lens manipulator that can be controlled by a user to insert a contact lens into the eye or remove it from the eye. Further embodiments include a display system that provides a user with dual images of the lens manipulator such that the user sees an optical illusion of the lens manipulator from a side view. This provides the user with an increased sense of control and safety when inserting or removing contact lenses. Additional embodiments can include a hands-free contact lens cleaning and storage system.

18 Claims, 27 Drawing Sheets

(56) References Cited

U.S. PATENT DOCUMENTS

| | | | |
|---|---|---|---|
| 4,201,408 A | | 5/1980 | Tressel |
| 4,221,414 A | | 9/1980 | Schrier |
| 4,286,815 A | | 9/1981 | Clark |
| 4,326,742 A | | 4/1982 | Ingram |
| 4,378,126 A | * | 3/1983 | Procenko .............. A61F 9/0061 294/1.2 |
| 5,050,918 A | * | 9/1991 | Kolze ................... A61F 9/0061 294/1.2 |
| 5,144,144 A | | 9/1992 | Borovsky |
| 5,572,785 A | * | 11/1996 | Tveit ........................ G02B 7/02 29/283 |
| 6,080,361 A | | 6/2000 | Borovsky |
| 6,652,015 B1 | * | 11/2003 | Carney ................... B25J 15/10 294/106 |
| D498,590 S | | 11/2004 | Borovsky |
| 6,868,963 B2 | | 3/2005 | Borovsky |
| 7,163,245 B2 | | 1/2007 | Wallock et al. |
| 7,168,746 B2 | * | 1/2007 | Py ........................ A61F 9/0061 294/1.2 |
| 7,503,605 B2 | | 3/2009 | Mears |
| 7,673,836 B2 | | 3/2010 | Wallock et al. |
| 7,914,056 B1 | * | 3/2011 | Peterman ............. A01K 1/0114 294/1.3 |
| 2006/0176570 A1 | | 8/2006 | Hennegan |
| 2007/0262596 A1 | | 11/2007 | Renard et al. |

\* cited by examiner

EYE CONTACT LENS INSERTION AND REMOVAL APPARATUS

CROSS-REFERENCE TO RELATED APPLICATION

This application claims the benefit of U.S. Provisional Application Ser. No. 61/955,409, filed Mar. 19, 2014, the disclosure of which is hereby incorporated by reference in its entirety, including all figures, tables and drawings.

BACKGROUND OF INVENTION

Contact lenses for the eye, commonly referred to as just "contacts," are a convenient and comfortable way of improving vision. They can eliminate the need for glasses and are particularly advantageous when other ocular devices are used, such as binoculars, diving masks, microscopes, sunglasses, protective eyewear, or other similar types of devices that would be difficult or impossible to use while wearing regular eye glasses. Certain medical conditions can also necessitate the wearing of contact lenses. Cataract surgery where an artificial lens cannot be implanted in the eye may require a patient to wear contacts. Contacts may also be required to treat certain types eye diseases, such as keratoconus or damage to the cornea caused by an injury or infection of the eye.

Typically, contact lenses are installed in or removed from the eye using one or more fingers. For installation, the contact lens is balanced on one finger and one or both lids of the eye are usually pulled back from the eye. A few drops of saline or other artificial eye fluid are dropped onto the lens. There should be a sufficient amount of fluid to allow cohesion, but not so much that the fluid washes over the lens and inhibits attachment. The contact lens is then gently pushed against the eye, where forces of cohesion and adhesion will cause the lens to attach to the eye and float on the thin layer of fluid on the surface of the eyeball. This process can be difficult and quite stressful for some people to perform. It requires manual dexterity and hand and eye stability to ensure that the contact lens is brought into sufficient proximity to allow attachment to the eye surface without causing accidental or painful contact with the cornea and sclera. Likewise, removal requires a steady hand and the ability to pinch or squeeze the contact to dislodge it from the surface of the eye.

There are devices that can assist with the insertion and removal of contacts. It can be difficult, however, to judge distances when using such devices close to the eye. Many utilize suction forces to hold the contact while inserting it or to pull the contact from the eye during removal. However, if the contact is not immediately released upon adhering to the eye, the suction force can cause painful contact with the cornea or sclera during installation and may even remove the contact instead of leaving it in place. It is also not uncommon for contacts to form a strong contact with the eye surface, particularly when too dry or when worn for protracted periods. If the suction of the device is too strong, it can damage the eye while the user is trying to remove a too-strongly adhered contact.

Another issue with contacts is the transmission of dirt, microorganisms, and other undesirable products to the eye. Usually these undesirable products are not seen, but can often be felt after the contact is inserted. Contacts are usually treated with cleaning and disinfecting solutions to reduce or eliminate unwanted dirt, protein build-up, microorganisms, etc. Cleaned contacts are then stored in individual wells and are retrieved with the fingers or, sometimes, another device before being inserted with fingers or a device. During transfer the contact can be dropped or dirtied, the fluid necessary for comfortable insertion can leak or drip out of the contact, or the contact can be torn, chipped, or otherwise damaged.

There is a need for a device that can aid in inserting and removing contact lenses. Such a device will, ideally, reduce the amount of manual dexterity required, prevent undesirable contact with the cornea or sclera of the eye, and release the contact immediately upon insertion or prevent excessive force on the eye if the contact is difficult to remove. It can also be beneficial for such a device to control the amount of fluid on the contact and ensure that the fluid remains in the contact lens vault during installation. A further advantage would be to provide a user with the ability to observe the device during installation and removal of contacts to enable a sense of safety and confidence when using the device. Observation can also provide an opportunity to inspect a lens prior to insertion. If such a device could be incorporated with a hands-free system of contact storage it would constitute a dramatic improvement in the use of contacts and could increase probable continued use of contacts.

BRIEF SUMMARY

The subject invention successfully addresses the above described disadvantages associated with insertion and removal of contact lenses in the eye and previously known devices and methods, and provides certain attributes and advantages, which have not been realized by these known devices. In particular, the subject invention provides embodiments of a "Contact Lens Insertion And Removal Apparatus" (CLIARA) and a method of use. The CLIARA employs a lens conveyer system that is novel and provides a safe and comfortable method for insertion and removal of contacts. A display system can be utilized in conjunction with the lens conveyor system to provide a user with a real-time, visual image of the process. Additionally, embodiments can utilize a storing and cleaning system for contact lenses that can be incorporated with the lens conveyor system, such that the entire CLIARA system can be operated without direct manipulation by the user's hands of the contact lenses.

The lens conveyor system can include a rod with a lens manipulator disposed in a lens sink over the rod. The rod can be manipulated by the user with a handle that operates a mechanism to bring the lens manipulator, on which a contact lens is supported, to the eye and deposits the lens onto the surface of the eye. The display system can utilize strategically placed viewing mechanisms, such as, for example, mirrors, guides, and/or cameras and display screens, to provide the user an image of the cup holder approaching the eye. The cameras can relay to the display screen for each eye an image of the lens manipulator as it nears the eye receiving the contact lens. The eye receiving the contact lens simultaneously sees the lens manipulator approaching. This dual imagery will create an optical illusion in the mind of the user of the lens manipulator approaching the eye from a sideways direction. It also allows a user to watch the entire process, which provides a sense of safety and control as the user manipulates the rod with the handle.

A storage and cleaning system can be incorporated with the lens conveyor system by including one or more storage wells for lenses. Each well can incorporate a cupped end that forms a seal with an opening in each well. When the storage well is aligned with the lens conveyor system, the rod can be advanced towards the well to automatically connect with the cupped end. As the rod continues to advance, the cupped end will enjoin with the lens in the well and bring it to the eye for deposit onto the eye surface. The wells can be fitted with various mechanisms for depositing or removing fluid from the well, as well as chemical and non-chemical methods of cleaning, disinfecting, or sterilizing lenses.

One advantage of the CLIARA and method of use of the subject invention is that certain embodiments provide an entirely mechanical, i.e., non-electrical, system for inserting and removing contact lenses. This allows the system to be portable, easy to manipulate, and to give the user complete control over the entire processes. That is not to say that the embodiments herein cannot be automated and it is possible that certain embodiments can be motorized. In addition, embodiments herein can be sterilized by any of a variety of methods or techniques, such as by chemical, thermal, radiation, and other techniques known in the art that are non-damaging to the materials of the embodiments of the subject invention and that do not adversely affect the lenses or user. In a particular embodiment, select components of the lens conveyor system can be removed from the CLIARA system and sterilized, such as, for example, with an autoclave.

Ideally, the CLIARA system will be calibrated by a medical professional. Such calibration can ensure, for example, that the rod advances to the eye only as far as necessary to deposit the lens, that the cupped end releases the lens at the appropriate time, and that other features are properly aligned, fitted, set, or otherwise customized to each specific user.

It should be noted that this Brief Summary is provided to generally introduce one or more select concepts described below in the Detailed Disclosure in a simplified form. This Summary is not intended to identify key and/or required features of the claimed subject matter. Other aspects and further scope of applicability of the present invention will also become apparent from the detailed descriptions given herein. It should be understood, however, that the detailed descriptions, while indicating preferred embodiments of the invention, are given by way of illustration only, since various changes and modifications within the spirit and scope of the invention will become apparent from such descriptions. The invention is defined by the claims below.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings. The drawings presented herein may not be drawn to scale and any reference to dimensions in the drawings or the following description is specific to the embodiments disclosed. Any variations of these dimensions that will allow the subject invention to function for its intended purpose are considered to be within the scope of the subject invention. Thus, understanding that these drawings depict only typical embodiments of the invention and are not, therefore, to be considered as limiting in scope, the invention will be described and explained with additional specificity and detail through the use of the accompanying drawings.

In FIG. 4B there is shown an embodiment of an overflow cup and an alternative embodiment of a face prop. FIGS. 4C and 4D illustrate embodiments of a compression element.

FIGS. 15A and 15B are photographs showing a lens manipulator approaching an eye (FIG. 15A) and the one image seen by a user through a display system (FIG. 15B), according to embodiments of the subject invention. FIG. 15C is another graphic illustration of what a user sees when the contact lens cup is approaching the eye. FIG. 15D is a graphic illustration of what a user sees in the opposite eye watching the lens system of the subject invention. FIG. 15E is a graphical illustration of how the brain combines the images so that the user perceives a combined image.

DETAILED DISCLOSURE

Figure 1:
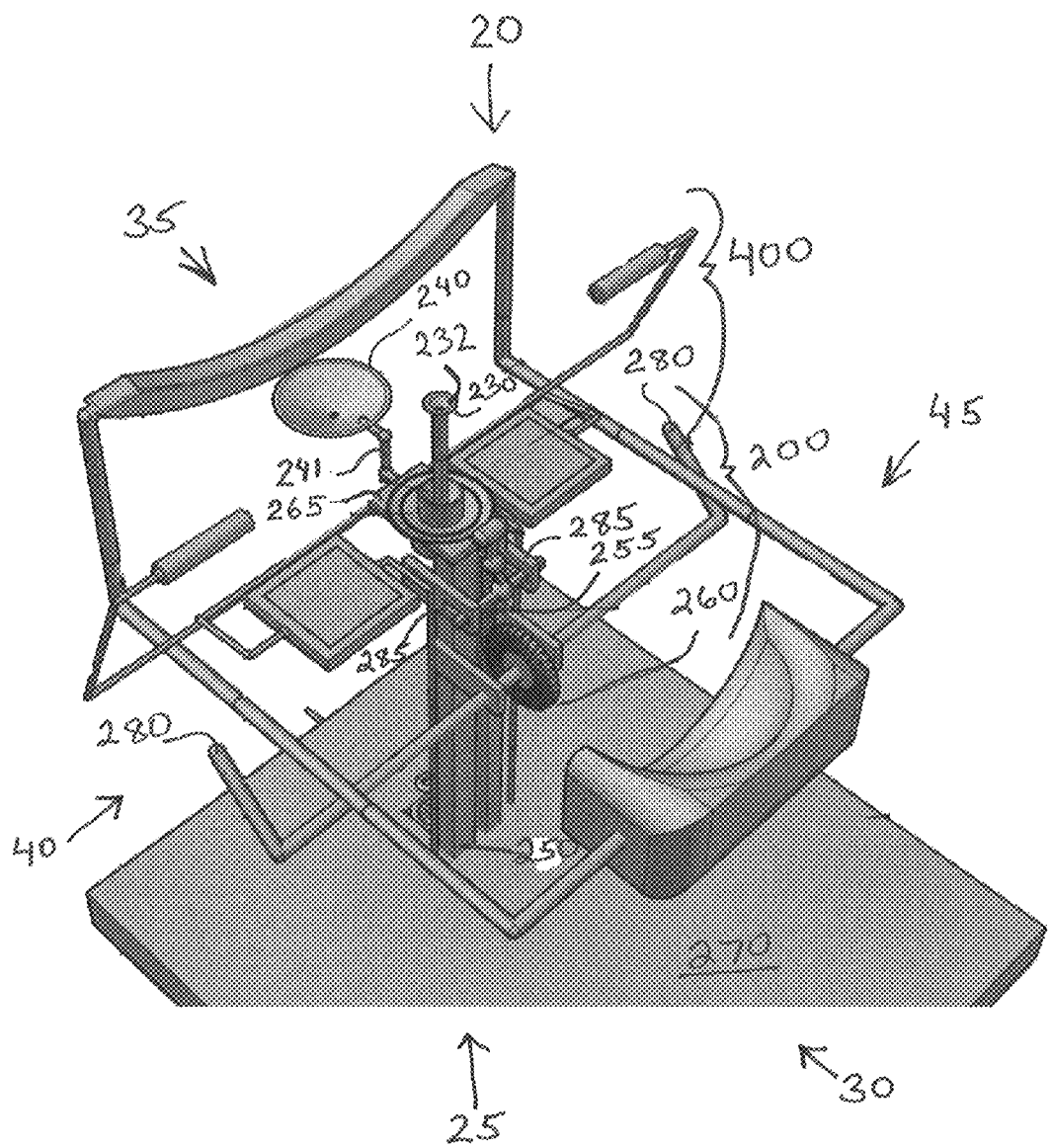
FIG. 1 illustrates an embodiment of a Contact Lens Insertion And Removal Apparatus (CLIARA).

The subject invention describes embodiments of a Contact Lens Insertion and Removal Apparatus, referred to herein as a CLIARA, and methods for using the apparatus. Specifically, the subject invention provides one or more embodiment(s) of a device that can be used to insert into or remove a contact lens from the eye and allows a user to visualize the process using images from two different angles. In particular embodiments, the devices of the subject invention allow a user to control a positioning mechanism while receiving simultaneous visual feedback of alignment in three dimensions from two orthogonal views. Alternatively, the two views are not orthogonal. Specific embodiments of the device can be configured for use with either rigid gas-permeable (RGP) lenses or soft lenses.

The following description will disclose that the subject invention is particularly useful in the field of optometry, in particular, devices used to insert or remove contact lenses from the eye. However, a person with skill in the art will be able to recognize numerous other uses that would be applicable to the devices and methods of the subject invention. While the subject application describes, and many of the terms herein relate to, a use for manipulating and controlling placement of contact lenses on the eye, other modifications apparent to a person with skill in the art and having benefit of the subject disclosure are contemplated to be within the scope of the present invention.

In the description that follows, a number of terms related to the invention are utilized. In order to provide a clear and consistent understanding of the specification and claims, including the scope to be given such terms, the following definitions are provided.

The terms "contact lens" and "lens" are used interchangeably throughout the application. It should be understood that both of these terms refer to any device attached directly to the eye to correct, alter, or otherwise change the vision of the eye. In general, it refers to such devices that are rigid, such as, for example, Rigid Gas-Permeable (RGP) contact lenses. Other more specific embodiments disclosed herein are utilized with soft contact lenses. Where appropriate the application will distinguish between embodiments utilized with each type of contact lens.

As used herein, and unless otherwise specifically stated, the terms "operable communication," "operable connection," "operably connected," "cooperatively engaged" and grammatical variations thereof mean that the particular elements are connected in such a way that they cooperate to achieve their intended function or functions. The "connection" or "engagement" may be direct, or indirect, physical or remote.

Also, reference is made throughout the application to the "proximal end" and "distal end." As used herein, the proximal end is that end closest to a user when a user is in position to receive a contact lens in the eye. Conversely, the distal end of the device is that end that is further from the user when the user is in position to receive a contact lens in the eye.

The present invention is more particularly described in the following examples that are intended to be illustrative only since numerous modifications and variations therein will be apparent to those skilled in the art. As used in the specification and in the claims, the singular for "a," "an" and "the" include plural referents unless the context clearly dictates otherwise.

Reference will be made to the attached figures on which the same reference numerals are used throughout to indicate the same or similar components. With reference to the attached figures, which show certain embodiments of the Contact Lens Insertion and Removal Apparatus, CLIARA 10, of the subject invention, it can be seen that the subject invention can include a lens conveyor system 200 and a display system 400. Further embodiments can include a storage and cleaning system 500. These systems will be described by reference to the proximal end 20, the distal end 25, the front side 30 (where a user stands), the back side 35 (opposite to where the user stands), the left side 40 and the right side 45 (which correspond to the left and right eye, when positioned at the front side). FIG. 1 illustrates these different areas on an embodiment of the invention.

Figure 2:
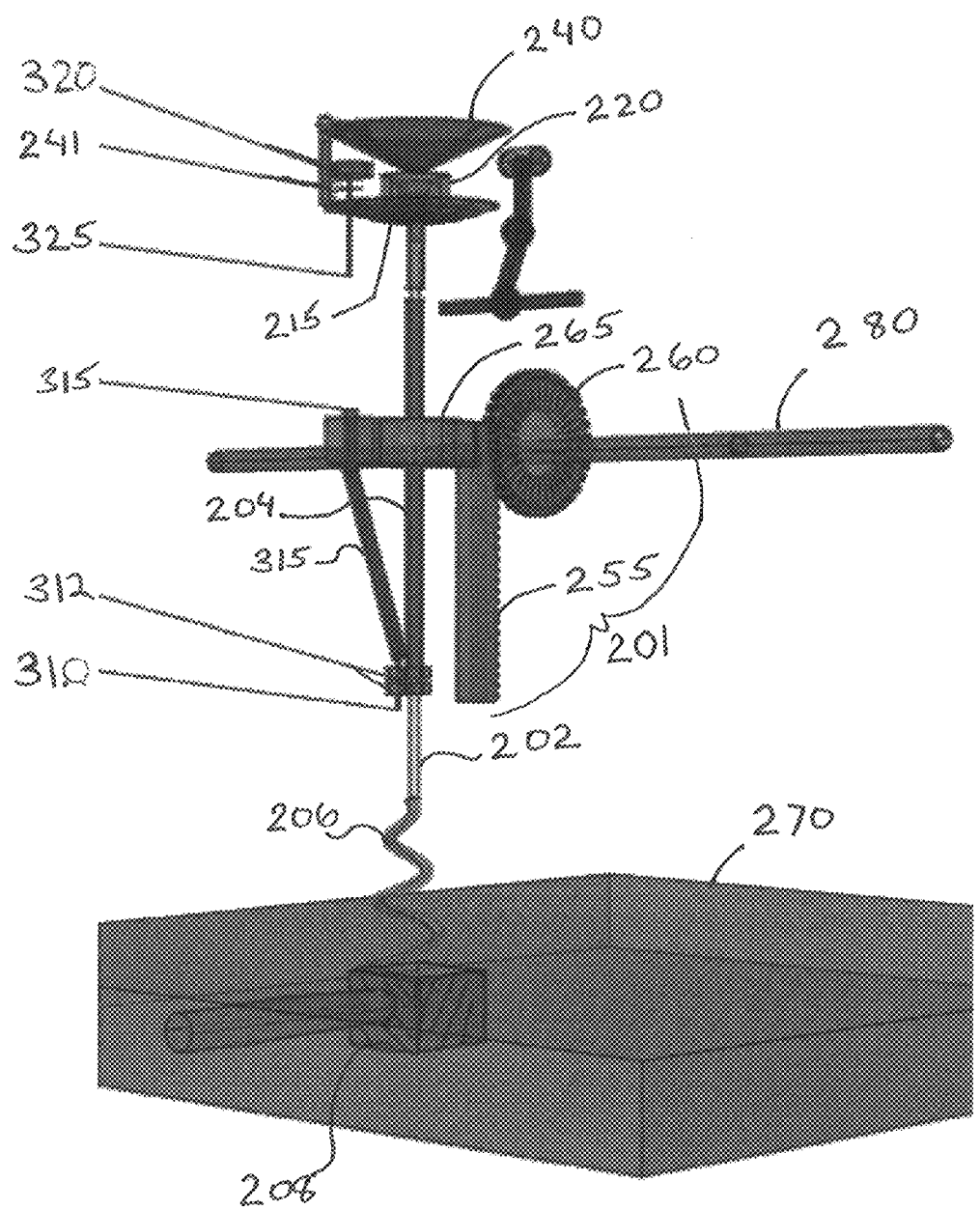
FIG. 2 illustrates an embodiment of a CLIARA with the tower support removed to better demonstrate the positions and interconnection of related components.
Figure 3:
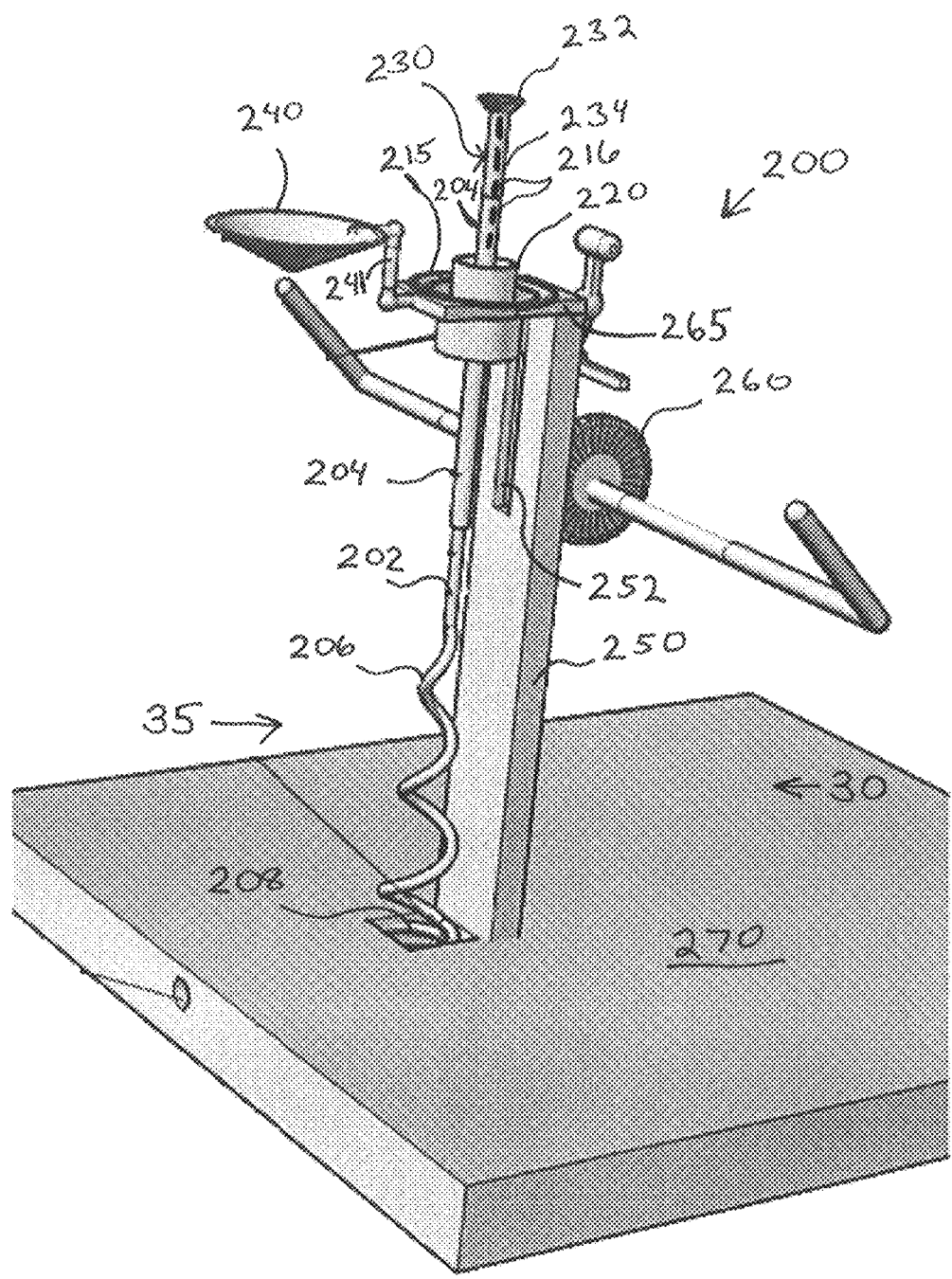
FIG. 3 illustrates an enlarged view of an embodiment of a CLIARA with the lens manipulator raised.

The lens conveyor system 200 can be comprised of several components designed to carry a lens 15 to the surface or cornea of the eye. The system can include an actuator mechanism 201, such as, for example, a linear actuator mechanism. FIGS. 2 and 3 illustrate the general components that can be used with embodiments of a lens conveyor system, where FIG. 2 shows the lens conveyor components without a support tower 250, which is shown in FIG. 3. In FIG. 2, there is shown a rod 202 disposed within a vertical rod sleeve 204. In one embodiment, the rod is movably secured within the rod sleeve. The rod can also be attached to a light source 208 capable of transmitting light through the rod. In one embodiment, at the distal end 25 of the rod, there is attached a light emitting mechanism 208 that projects light into the end of the rod. In a specific embodiment, the light emitting mechanism includes a fiber optic cable 206 that operably communicates with the rod, such as, for example, being attached at or about the distal end 25 to the rod. The fiber optic cable can likewise operably communicate with a light emitting source 208 and transmit the light to the rod. Ideally, the fiber optic cable 206 or other light emitting source operably communicates with the rod in a fashion that does not inhibit the rod from moving in a proximal or distal direction. FIGS. 2 and 3 illustrate an embodiment where a fiber optic cable is coiled, so that it can move cooperatively with the rod.

In one embodiment, the rod comprises a transparent material or one capable of transmitting or conveying light along or through the length of the rod. Any of a variety of materials can be utilized for a rod through which light can pass, including, but not limited to, glass, acrylics, plastics, silicon, ceramics, and other materials or combinations thereof. Certain materials are specifically suited for light transmission, such as, but not limited to, polycarbonates and high-purity silica, and could also be utilized with embodiments of the subject invention.

Typically a rod comprises a rigid or semi-rigid material. But a rod could incorporate any of a variety of liquids, gels, gases, semi-solids, or other non-rigid materials, or combinations thereof. The use of materials and substances that are capable of transmitting or conveying light is a well-developed field. It is within the skill of a person trained in the art to determine which of one or more materials would be suitable for a rod according to the subject invention. Such variations, which provide the same function in substantially the same way with substantially the same result, are within the scope of this invention.

Figure 11:
FIG. 11 is a photograph of an enlarged view taken from the top of the lens sink of the embodiment shown in FIG. 9.

As will be discussed below, the light is transmitted to at or about the proximal end of the rod, so that it can act as a guide 210, which can be seen by a user during the lens insertion or removal process. FIG. 11 shows an example embodiment of the end of the rod as seen by a user within a lens sink, prior to insertion or removal of a lens. The use of a light transmitting rod is a convenient way to combine two aspects of the subject invention. However, the rod does not have to be light transmitting. It is possible for a guide 210 light source to be derived or incorporated by other means, known to those with skill in the art. For example, a beam of light could be directed into the lens sink or another area of the CLIARA 10 to guide a user. In fact, it is possible for a guide to be something other than a light source. Various types of indicators known in the art could also be located on the CLIARA, such as, but not limited to, glowing or shining areas, reflectors, colored indicators, or any other devices and methods that can be used as a visual cue. Such variations which provide the same function as a lighted rod, in substantially the same way, with substantially the same result are within the scope of this invention.

The rod sleeve 204 can act as a support for the rod. The rod sleeve can also be an insulator to aid in light transmission by the rod. There are several factors that dictate the length of a rod sleeve, which will become apparent from the description below. In one embodiment, the length of a rod sleeve is less than the length of the rod, such that the rod extends from the sleeve at one or both the proximal and distal ends, as shown in FIG. 2. In another embodiment, the rod extends from the sleeve at least from the proximal end, so that it can engage with a lens manipulator 230. One purpose of the sleeve is to carry the rod proximally, as described below. Thus, the length of the sleeve can depend upon the distance that the rod must travel in operation.

The embodiments shown in FIGS. 1, 2, 3, and 4A show a substantially linear or straight rod and rod sleeve configuration. This can be the most expedient configuration in order that the rod and rod sleeve can be moved proximally in a substantially straight line. There are several reasons for this, one being that it helps maintain a desired amount of contact lens fluid in the concave side of the contact lens 15, referred to herein as the lens vault 17. Because the rod transports a contact lens in a generally linear proximal direction, a linear rod can be most efficacious. However, it is possible for the rod and rod sleeve to have a configuration that is not straight, or not entirely straight, and still be able to transport a contact in a preferred direction.

In one embodiment, the rod and rod sleeve can be supported in a non-vertical direction or at an angle relative to a horizontal plane. The rod and rod sleeve can be engendered with flexibility combined with shape-memory characteristics. When the rod and rod sleeve are moved proximally, they can slide through a mechanism that temporarily bends them from the original angle and redirects them proximally. The shape memory will cause them to immediately resume a linear configuration as they exit the bending mechanism. Other techniques and methods could be used whereby the rod and rod sleeve are not required to be linear or are not required to be maintained in a vertical position, as shown in the figures. Such variations which provide the same attributes, functions, and advantages as the embodiments disclosed herein, are within the scope of this invention.

Figure 4A:
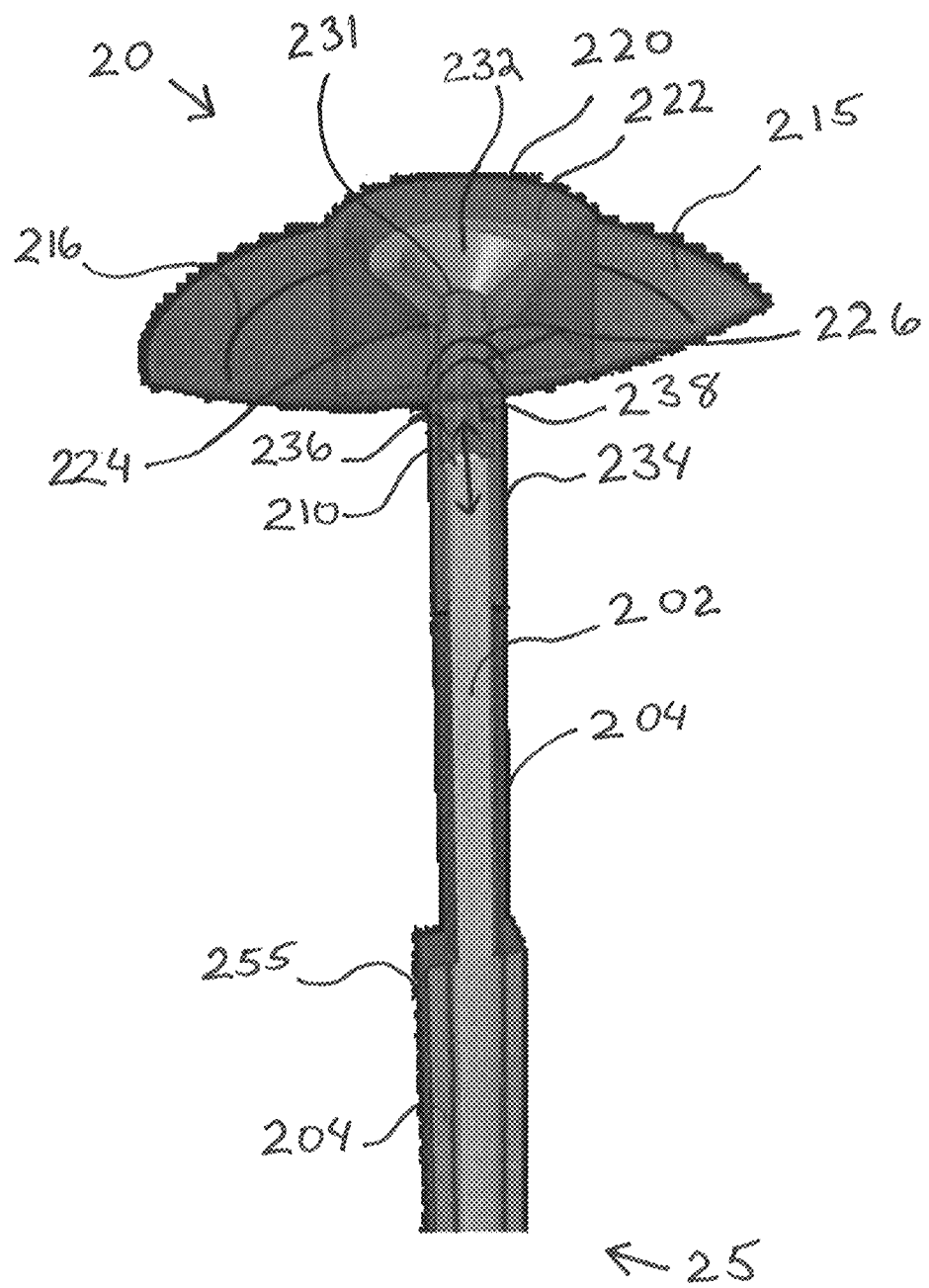
FIGS. 4A, 4B, 4C, and 4D illustrate an enlarged view of a portion of a lens conveyor system, according to embodiments of the subject invention. Specifically shown in FIG. 4A are the lens manipulator, rod, rod sleeve, lens sink, and guide mirror.
Figure 4B:
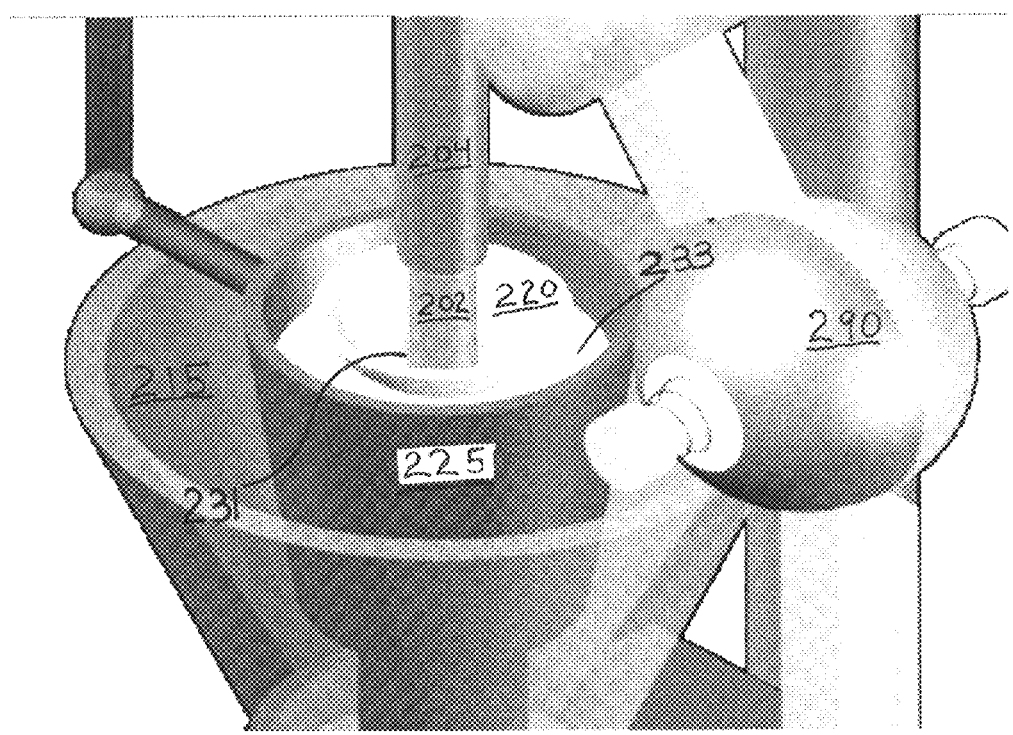
Figure 5:
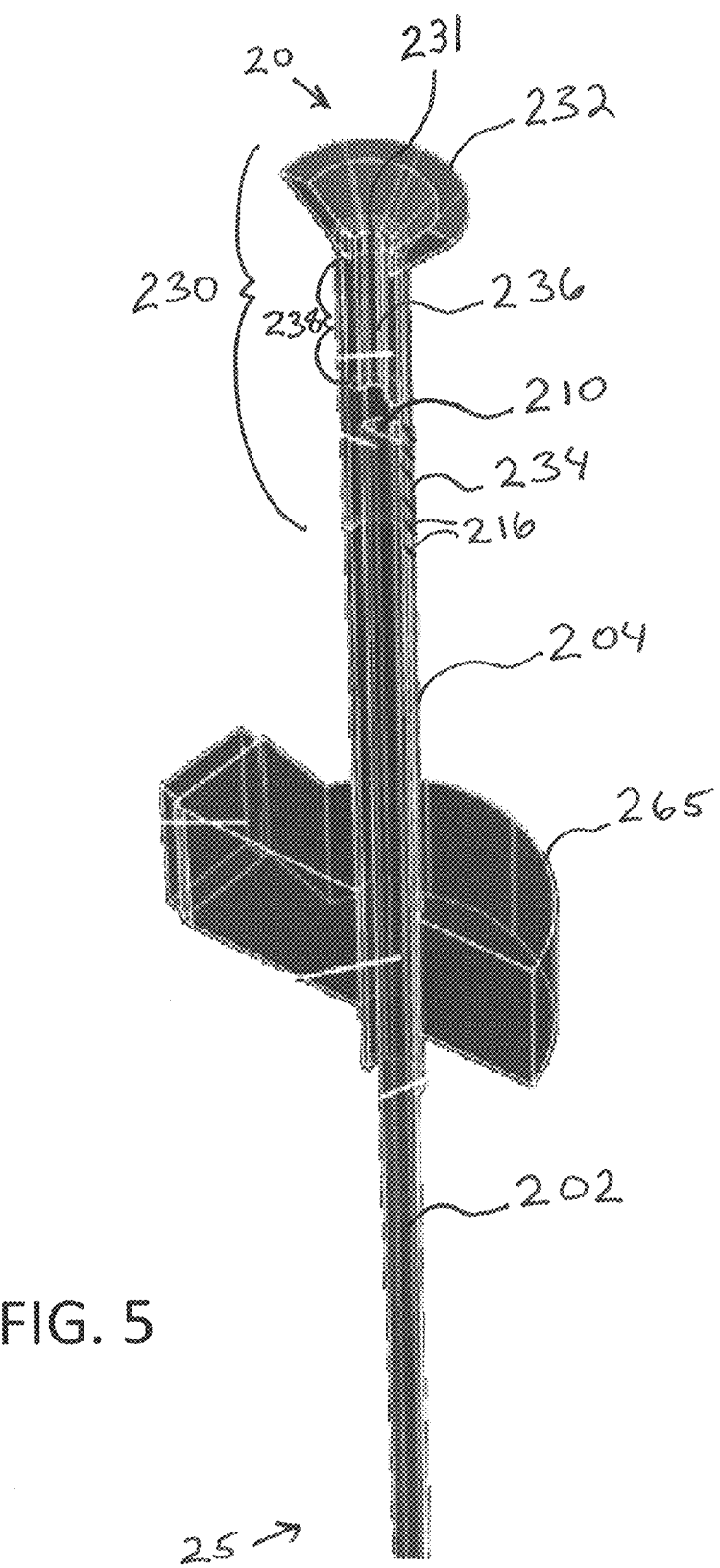
FIG. 5 illustrates an enlarged view of a portion of a lens conveyor system, including a rod sleeve stage, according to embodiments of the subject invention.

At the proximal end of the rod, there can be located a lens manipulator 230. FIGS. 4A and 5 illustrate general embodiments having a tubular form with a proximal end 20 portion in the shape of a concave suction cup 232 and a distal end 25 portion as a tube 234 with a channel 236 therethrough that communicates the distal and proximal ends of the tubular form, such that the channel opens to form a pore 231 into the concave area or interior 235 of the suction cup portion, so as to communicate the distal end of the tube with the suction cup interior, an example of which is shown in FIGS. 4A, 4B, and 5.

Figure 6A:
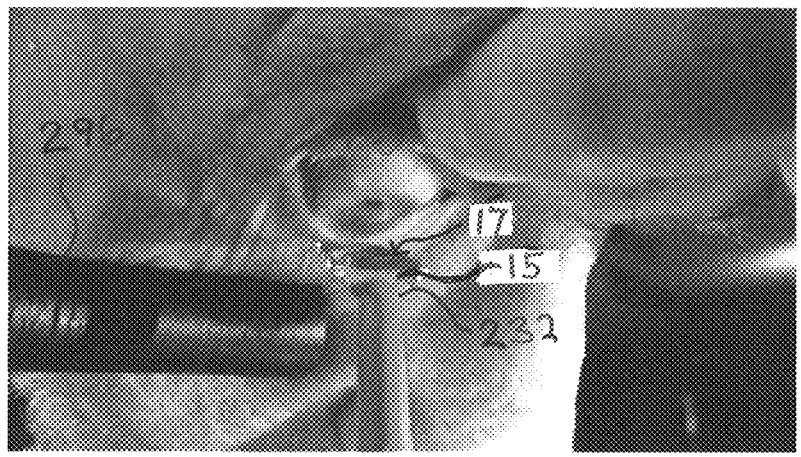
FIGS. 6A, 6B, and 6C are sequential photographs showing a lens manipulator inserting a contact lens onto the cornea of a user.
Figure 6B:
Figure 6C:

In one embodiment, the proximal end 20 of the rod 202 is removably joined with the distal end 25 of the channel 236. In a further embodiment, the lens manipulator 230 comprises sufficient weight to ensure that during operation it remains seated or resting on the proximal end 20 of the rod 202. In a particular embodiment, the rod is friction fit into the channel, where the friction fit is sufficient to pull the lens manipulator away from a contact lens 15 once the lens is deposited onto the eye. Typically, a contact lens being deposited on the eye is stabilized with the suction cup, but there is little or no actual suction force with the contact lens. More specifically, the contact lens can sit on the cup, but is not actively secured to the cup except, perhaps, by surface tension forces. This allows the rod to carry the lens manipulator towards the eye when it moves proximally and, further, allows the suction cup to be easily removed from the contact lens once the lens is deposited on the eye. Thus, the lens manipulator can temporarily stabilize a contact lens while it is transported towards and deposited on the eye. Typically, the comparable shapes of the cup 232 and the contact lens are sufficient to hold the contact lens in place on the suction cup as it moves proximally. Sufficient fluid deposited into the lens vault 17 can also cause the contact lens to easily transfer to the surface of the eye when in sufficient proximity to the surface of the eye. Ideally, there is sufficient fluid deposited into the lens vault that the fluid reaches the eye before the contact lens does, so that normal forces of surface tension between the contact lens, fluid, and the eye will transfer the contact lens from the suction cup to the surface of the eye. However, some individuals may prefer to use less fluid, which will require the contact lens to make slightly more contact with the eye for deposition. FIGS. 6A, 6B, and 6C illustrate an example of this process, whereby the cup 232 with a contact lens thereon is advanced towards the eye. FIG. 6B shows how the contact lens "floats" on the surface of the eye as the fluid therein makes contact with the surface of the eye. FIG. 6C illustrates the cup being withdrawn after the contact lens is on the eye.

The size of the cup 232 can vary, but ideally will have a linear diameter, i.e., the diameter across the proximal end of the cup, that is smaller than a contact lens thereon. In one embodiment, the linear diameter of a cup is between approximately 4 mm and approximately 8 mm. In a specific embodiment, the diameter of a cup is between approximately 5 mm and approximately 7 mm. In a more specific embodiment, the diameter of the cup is approximately 6 mm. Additionally, while the spherical diameter of a cup can vary, it can, but is not required to, match the spherical diameter of a contact lens.

Another important feature of the lens manipulator is that it can also be used to extract or remove a contact lens 15 from the eye. The embodiments described above are particularly suited for removing RGP contact lenses because the rigidity is conducive to forming a suction force with the cup 232 on the lens manipulator 230. With this embodiment, the cup 232 can be moved towards an eye, which has a RGP contact lens thereon, and the cup can be gently pushed against the lens to deform the cup 232 until a suction force is created between the RGP contact lens and the cup. The maximum amount of suction force with which the cup 232 can attach to a contact lens can be dependent upon at least two factors. The first factor is the area of the concave cup and the second factor is the channel volume 238 between the proximal end of the rod and the distal end of the channel.

It is well-known in the art that the force of suction is determined by the formula: F=AP, wherein F=force generated, A=area under the suction cup, and P=pressure achieved inside the suction cup after evacuation of the air under the suction cup, usually achieved by deforming the cup against a surface to evacuate the air between the cup and the surface. In the embodiments of the subject invention, the amount of suction force that can be generated by the cup is dependent upon the channel volume 238 behind the cup, indicated in FIG. 4A, because that volume of space cannot be evacuated by deforming of the suction cup on a contact lens. Thus, there will remain an amount of air in the channel volume, even after the area under the suction cup is evacuated or partially evacuated. The greater the amount of channel volume, i.e., air remaining under the suction cup, the lower the maximum suction force that can be achieved. In one embodiment, the distance to which the rod is inserted into the channel from the distal end dictates the amount of channel volume 238.

This relationship between the rod, channel volume, and suction force provides the advantageous ability to adjust the maximum force that can be exerted by the suction cup by varying the distance of the rod into the channel 236 and, thus, varying the channel volume 238. FIGS. 4A and 5 illustrate how the rod slides into the lens manipulator and the arrows in FIG. 4A indicate that the rod can move in either direction to control channel volume.

In this way, the CLIARA 10 can be adjusted by a medical professional to the requirements of an individual patient. This can be particularly beneficial for removing a contact lens, where the suction cup is actually pressed against the RGP contact lens to create a suction force sufficient to remove the lens from the eye. By adjusting the depth of the rod 202 in the channel 236, the medical professional can adjust the maximum amount of pressure that can be created under the suction cup. This can prevent the suction cup from damaging the eye if the contact is adhered too strongly to the surface of the eye.

There can also be one or more compression elements 245 between the rod sleeve 204 and the tube 234. A compression element can be any device or mechanism that allows the distal end 25 of the tube to be temporarily moved or pushed closer to the proximal end 20 of the rod sleeve, if a pre-determined amount of pressure is applied to the lens. As discussed above, the CLIARA can be adjusted so that the cup 232 is inhibited from applying undesirable force against the eye as it removes or installs a contact lens 15. In the event that a lens conveyor system 200, in particular the tube, becomes improperly adjusted, altered, or changed, the compression element can provide a safety mechanism by which the cup can be inhibited from exerting undesirable force or pressure against the eye.

Figure 4C:
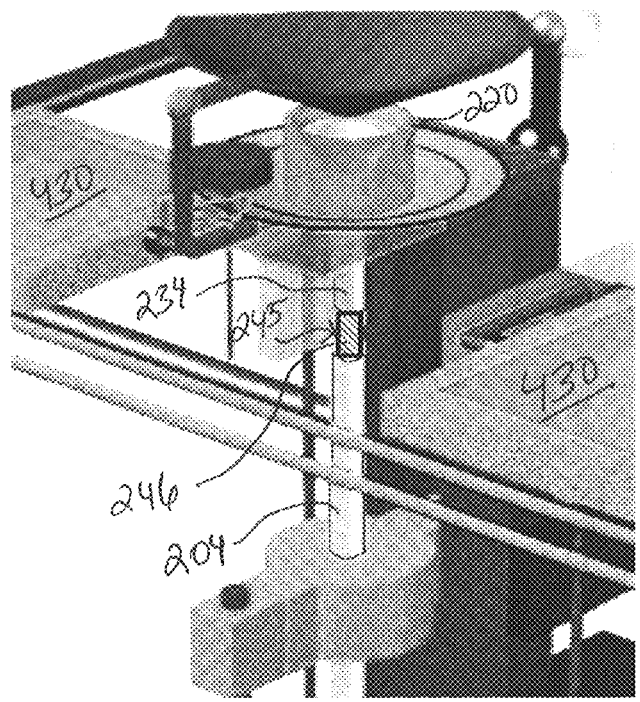
Figure 4D:
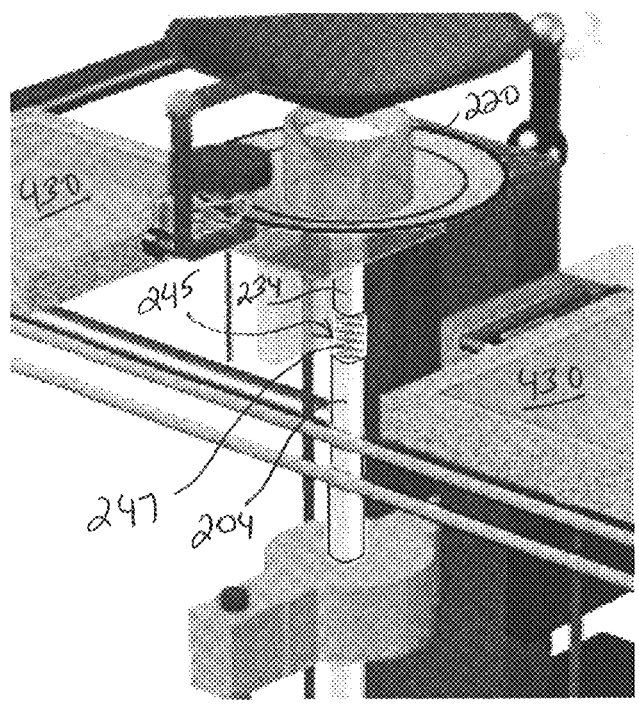

In one embodiment, a compression element 245 is a tube or ring of flexible material 246 that goes around, or at least partially goes around, the rod 202 and is between the rod sleeve 204 and the tube 234. One example of this is shown in FIG. 4C. A flexible material suitable for such use can be, but is not limited to, elastic foams, silicone, rubber, plastics, textiles, and other materials or combinations thereof. In another embodiment, a compression element 245 is a spring-like mechanism 247, such as shown, by way of non-limiting example, in FIG. 4D. A person with skill in the art will be able to determine an appropriate material, mechanism, or combination thereof that would be suitable for a compression element. Such variations are within the scope of this invention.

In one embodiment, the lens manipulator is fixedly attached to the rod. However, it is possible for a lens to form a stronger than average force of attachment to the surface of the eye. This can be caused by a variety of factors, most often due to an eye surface that is not sufficiently wet. When this happens it can be difficult to remove the lens from the surface of the eye. Unfortunately, this may not be determined until after the cup 232 has been attached to the contact lens on the eye. In these situations, it can be advantageous for the lens manipulator 230 to be easily removable from the rod end, so that excessive force is not applied to the eye. In one embodiment, the weight of a lens manipulator can ensure that it remains on the rod. In an alternative embodiment, the lens manipulator is friction fit onto the proximal end of the rod. In either case, the friction fit and/or the weight is sufficient to pull the lens manipulator away from the eye after a contact lens has been inserted onto an eye and to inhibit any contact lens fluid from draining out of the distal end of the channel. If the lens manipulator receives a pre-determined amount of resistance as it moves away from an eye, the lens manipulator will slide off of the rod end, exposing the distal end of the channel. By opening the distal end of the channel 236, the vacuum force exerted by the cup is negated and the lens manipulator will release the contact. In another embodiment, an emergency release system 300 can be incorporated with the CLIARA. The details of an emergency release system are provided below.

The materials utilized for the manufacture of a lens manipulator should be selected with an understanding of the functions performed by each part of the lens manipulator. In one embodiment the entire lens manipulator is formed from the same one or more materials. In an alternative embodiment, different parts of sections of the lens manipulator are formed of more than one material or of different materials. In one non-limiting example, the distal tube end 234 is formed of a rigid or semi-rigid material that can form a sufficient friction fit with the rod, but still be adjustable within the channel, as discussed above, while the cup is formed of a relatively soft or easily deformable material. In another non-limiting example, the entire lens manipulator can comprise an easily deformable material and the tube end can be covered with a more rigid material to support the tube end and aid in adjustability. In yet another non-limiting example, the material selected for a lens manipulator can have a durometer, or hardness value, that varies with the density and/or thickness of the material. Thus, the tube end 234 can be made thicker and thus have a higher durometer, i.e., less flexibility, than the cup, which can be made less dense or with a thinner layer of the same material, giving it a lower durometer, i.e., more flexibility. Alternative embodiments, or variations on these examples, that provide the same function, in substantially the same way, with substantially the same result are within the scope of this invention.

The lens conveyor system 200 described above is particularly useful with RGP (Rigid Gas Permeable) contact lenses because the rigidity of the lens allows for the formation of a suction force between the cup 232 and the lens. The ability to create a suction force depends upon the cup edges being initially able to conform to the surface of the RGP lens to create a seal. However, softer lenses have a more deformable surface, which can make it difficult or impossible for the cup 232 to form a seal sufficient to form a suction force for removal. Removal of softer lenses from the eye can require the cup to attach to the lens by a different method or device.

More specifically, the suction force between the contact lens and the cup can be generated by a vacuum system that pulls the lens towards the cup, rather than the cup being forced against the surface of the contact lens.

The lens conveyor system 200 can be modified to induce a negative-pressure behind the cup 232 that pulls a contact lens towards the cup. The negative-pressure suction force can be used for attachment of the cup to a soft contact lens. In one embodiment, the rod 202 is tubular. The proximal end 20 can be operably connected to the lens manipulator, as described above. The distal end 25 can be operably connected to a pump 228 capable of pulling air through or creating a vacuum with the tubular rod. Pumps are well-known in the art and any variations suitable for use with the embodiments of the subject invention are within the scope of this invention. In one embodiment, the pump is electrically operated. In another embodiment, a pump and a light source are both connected to the rod, which is illustrated, for example, in FIG. 17. This can allow the rod to emit light into the lens manipulator, as previously described, but also allows the pump to pull air through the tube to create suction force at the cup end. The amount of air, i.e., the suction force, to be pulled through the tubular rod can, of course, vary depending upon a particular user. As with the suction cup force described above, the amount of vacuum force necessary to attach the cup to a soft contact and remove it from an eye can be determined by a medical professional, preferably one who specializes in ophthalmology or optometry. In a specific embodiment, the pump can be calibrated to provide an adjustable level of maximum suction force. When the maximum level is detected by the pump or related sensors attached thereto, the pump will cease operating so that it does not exceed the maximum suction force. If the amount of suction force drops below the maximum level, the pump can restart operation and pull air through the tube until the maximum suction level is reached. A person with skill in the art would be aware of any of a variety of pumps that could be calibrated to ensure that a maximum suction force threshold is not exceeded. Such variations are within the scope of this invention.

Figure 17:
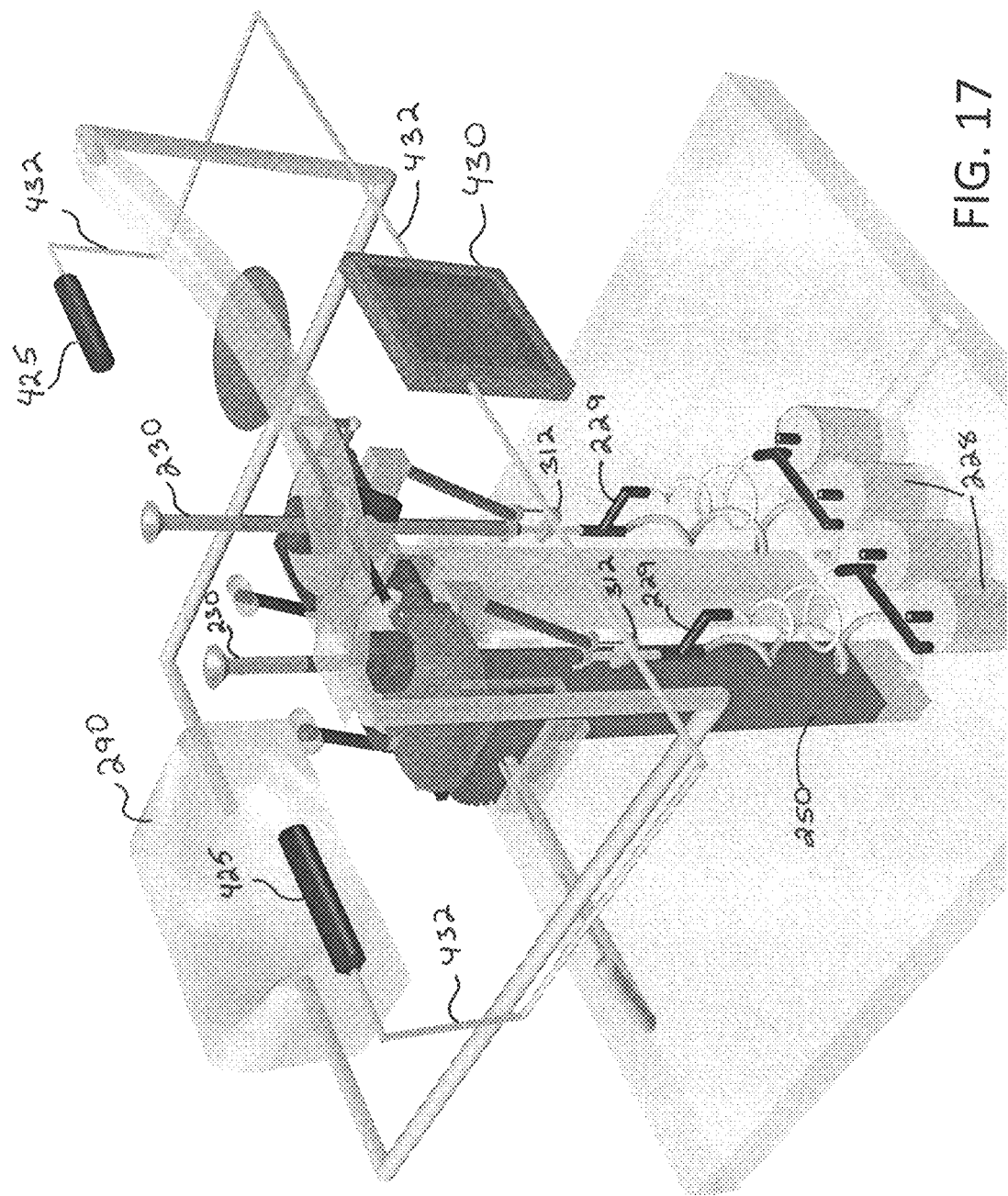
FIG. 17 is an illustration of an alternative embodiment of a CLIARA having a vacuum pump for creating suction in a cup on the lens manipulator. Also shown is an alternative placement for an electronic display screen.

In a further embodiment, the light source and pump can be connected to the rod by any of a variety of techniques and devices known in the art. In a particular embodiment, a dual connector 229 "T" or "Y" connector can be utilized to attach the light source and the pump to the tubular rod. FIG. 17 illustrates an example of a lens conveyor system having a light source and pump operably connected to a tubular rod by means of a connector. Other methods of connection, which provide the same functionality or substantially the same results are within the scope of this invention.

The factors that can be considered by those skilled in the art with regard to the choice of materials for a rod of the subject invention have been discussed above and are reasserted here with regard to the tubular rod embodiments. In a particular embodiment, the tubular rod is a translucent material. In a specific embodiment, the tubular rod is comprised of acrylic. Other materials known to those with skill in the art can also be utilized and are within the scope of this invention.

If a contact forms a stronger than usual attachment to an eye, it can be necessary to disengage the cup from the contact lens surface to prevent pain or injury. With the vacuum attachment described above, this can usually be accomplished by turning off the pump, which eliminates the suction force against the contact lens. The resiliency of the contact lens will cause it to deform slightly when suction is eliminated, allowing it to disengage from the cup. In one embodiment, the pump can be configured to exert a back-pressure into the rod that encourages the contact lens to disengage from the cup.

To deposit or extract a contact lens, the lens manipulator must necessarily be brought into proximity with an eye, as demonstrated in FIGS. 6A-6C. Preferably the lens manipulator will move in a steady, controlled manner towards the eye. Understandably, it can be preferable for the head and eyes to be held in a stable, relatively non-moving position while the lens manipulator approaches the eye. Most people tend to flinch or squint when an object approaches the eye, particularly when unexpected. This can be minimized if the user can control the approach of the lens manipulator to the eye.

Figure 7A:
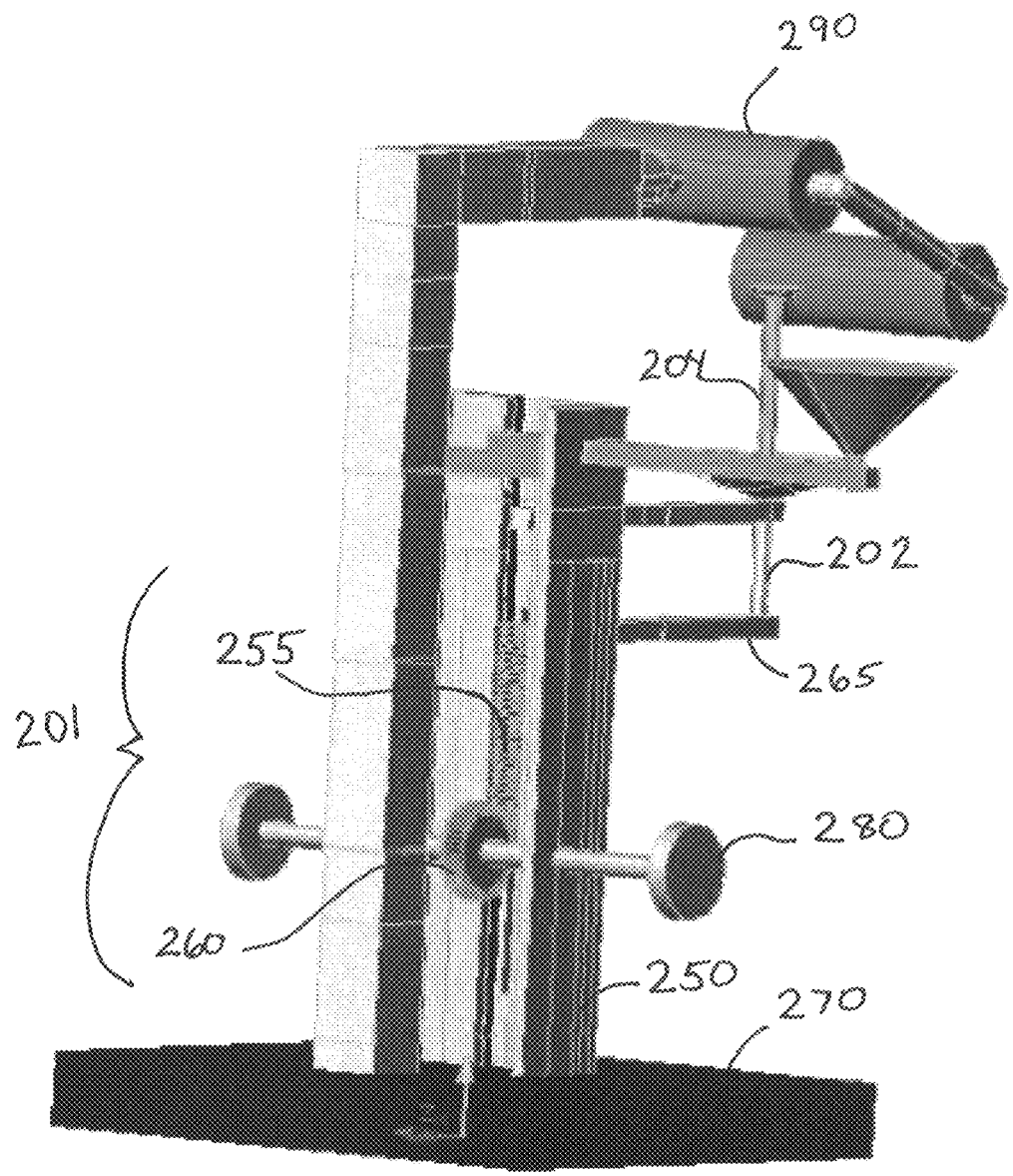
FIGS. 7A and 7B illustrate an alternative embodiment of a CLIARA having an alternative support tower configuration.
Figure 8:
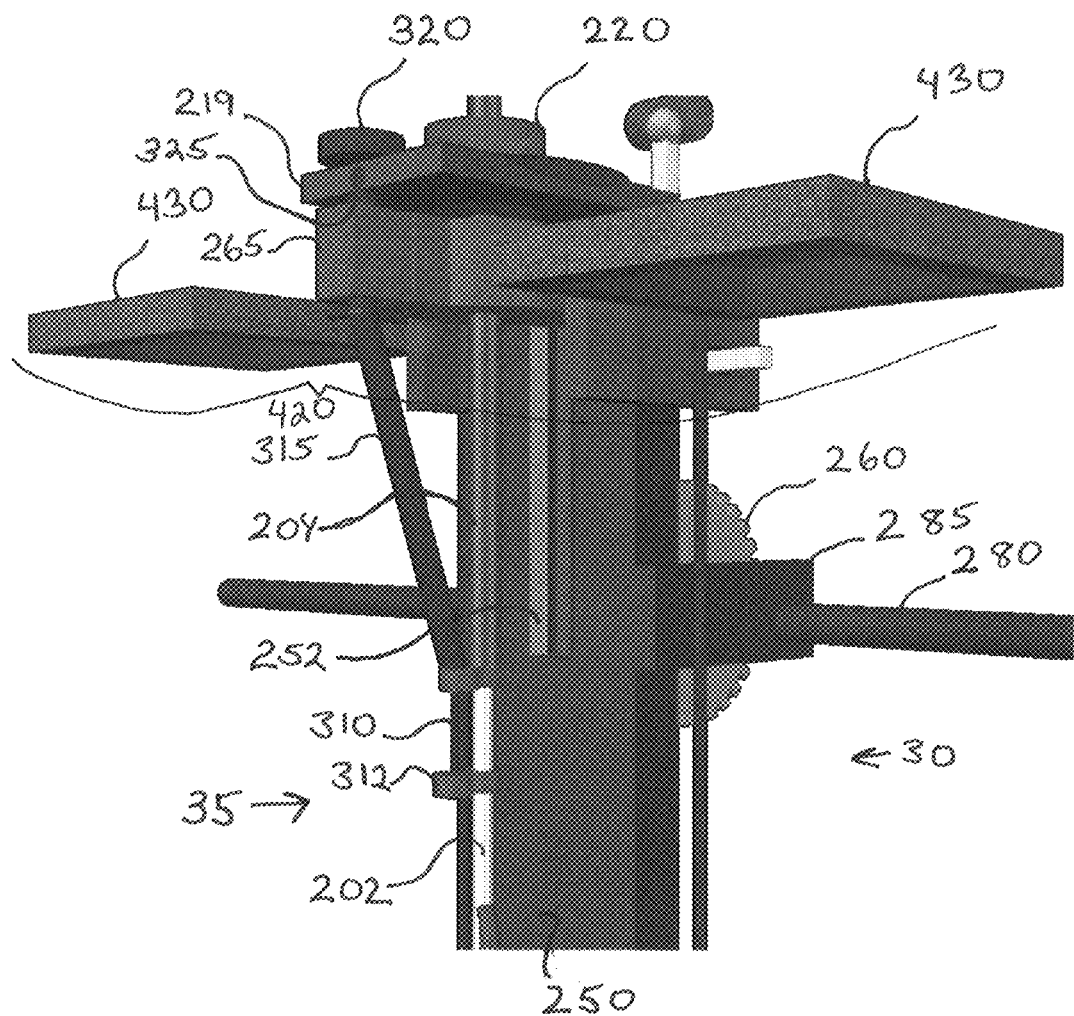
FIG. 8 is an enlarged, partial view of an embodiment of a CLIARA having an emergency release system.
Figure 14:
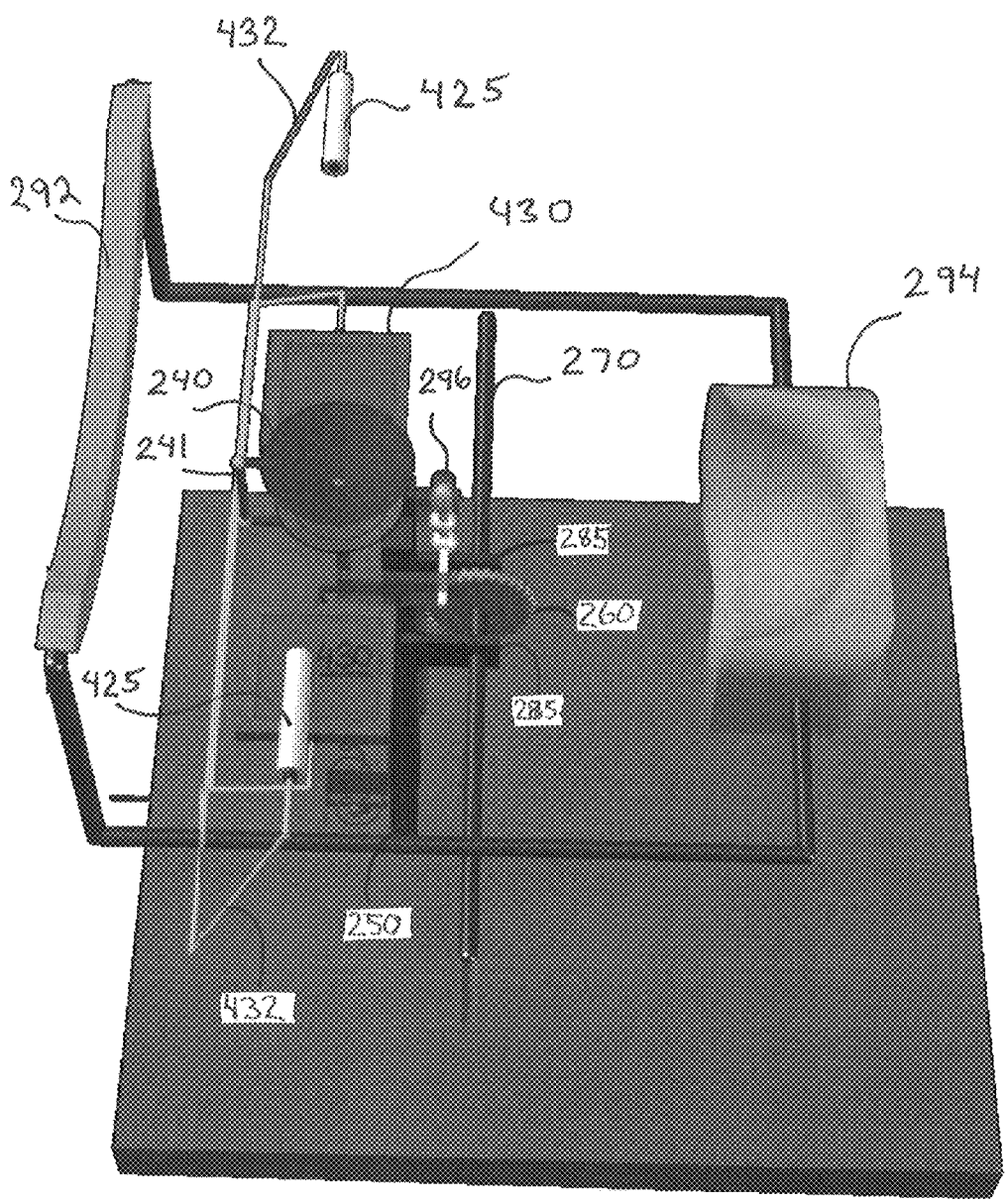
FIG. 14 is a left side top view illustration of another configuration of a CLIARA.

In one embodiment, the rod sleeve 204 is operably attached to an actuator mechanism 201 that raises and lowers it in a steady, controlled manner. In one embodiment, described above, raising and lowering the rod sleeve will simultaneously raise and lower the rod 206 and lens manipulator 230. It can be helpful for the actuator mechanism to be controlled by the user to provide a sense of safety and comfort to the user during the process. In one embodiment, the actuator mechanism 201 includes a generally vertical support tower 250 that holds a rack 255 and pinion 260, examples of which are shown in FIGS. 7A, 8 and 14. The rod sleeve 204 can be connected to the rack and is raised and lowered by operation of the pinion. Rack and pinion systems are typical linear actuator mechanisms 201 that are well-known in the art and generally comprise a stationary toothed gear or pinion 260 that can be rotatably engaged with a linear rack 255 to cause the rack to move in the direction that the pinion is rotated.

FIG. 2 shows an embodiment of the device of the subject invention without the tower in place, just to illustrate the relationship between the rack, pinion, and the rod sleeve. In the embodiment shown in this figure, the rod sleeve is operably connected to the rack by a stage 265. When the rack is moved the stage is likewise moved, which moves the rod sleeve affixed thereto and the rod fixedly attached through the rod sleeve. In one embodiment, the rod sleeve is fixedly attached to the stage. However, certain embodiments, described in more detail below, include an emergency release system 300. Thus, an alternative embodiment can have a rod sleeve that is slidably attached through the stage, such that a friction fit holds the rod sleeve in place until such time that the emergency release system is activated to slide the rod sleeve through the stage.

The support tower 250 can hold the rack, pinion, and stage in the appropriate configuration for operation. In one embodiment, the tower is securely attached to a base plate 270 at the distal end 25. In a further embodiment, the support tower has a conduit 252, illustrated, for example, in FIGS. 3 and 8. The conduit can provide a pathway by which the rack and stage can be moved up and down. The pinion can be secured to the tower so that it maintains a stationary, but rotatable position on the tower and can be operably engaged with the rack.

Figure 7B:
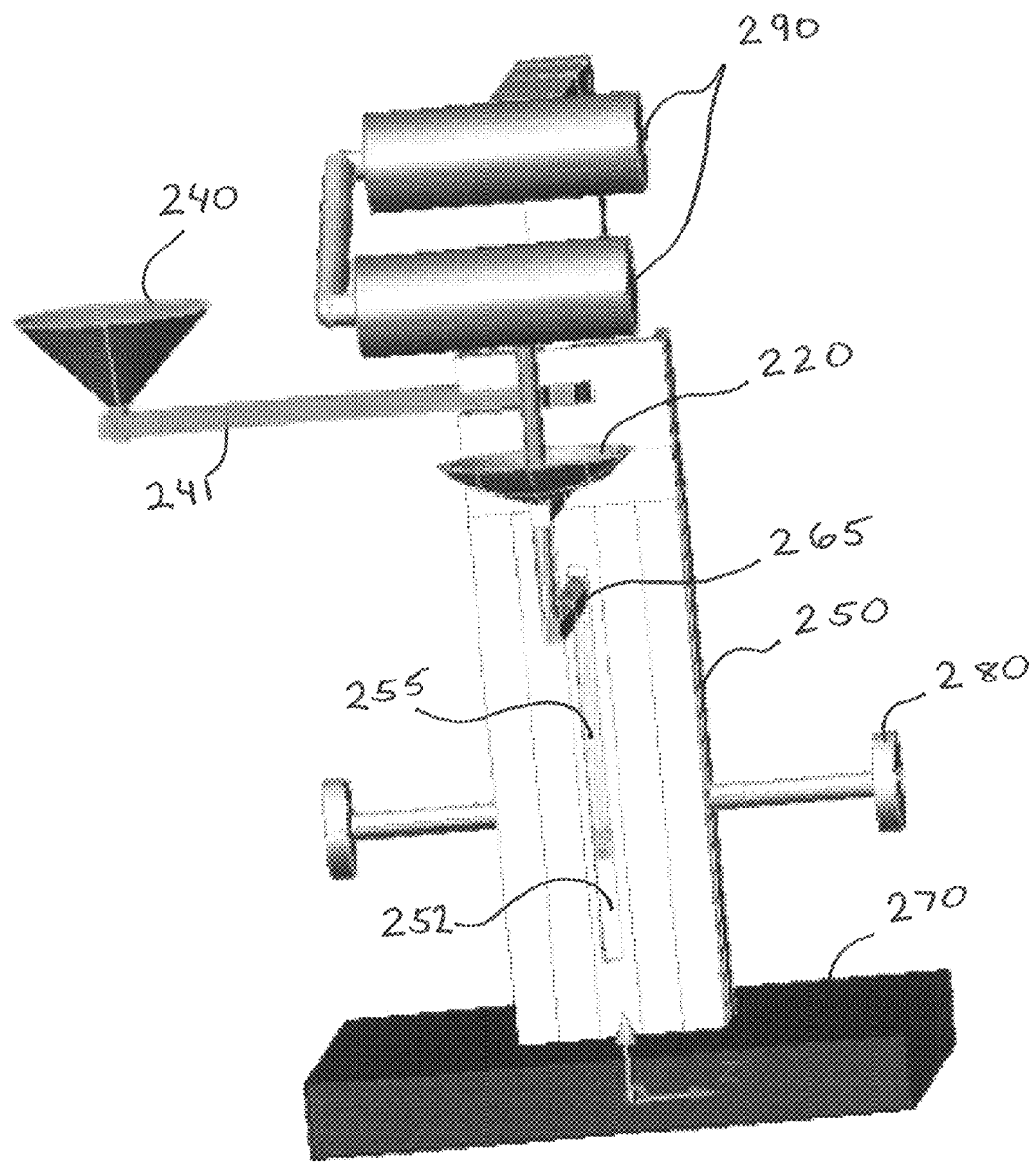
Figure 9:
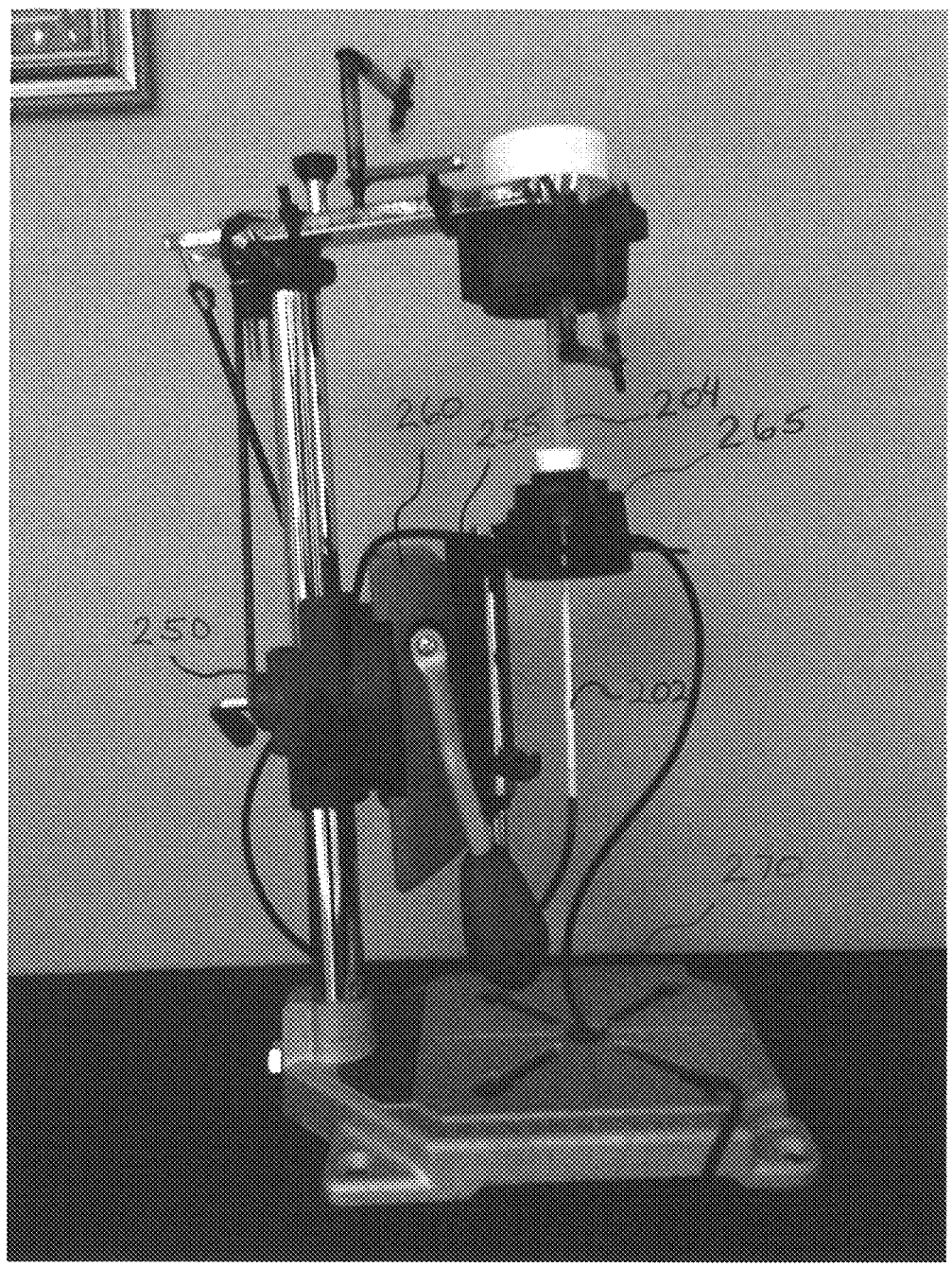
FIG. 9 is a photograph of yet another embodiment of a CLIARA utilizing an alternative support tower configuration.
Figure 10:
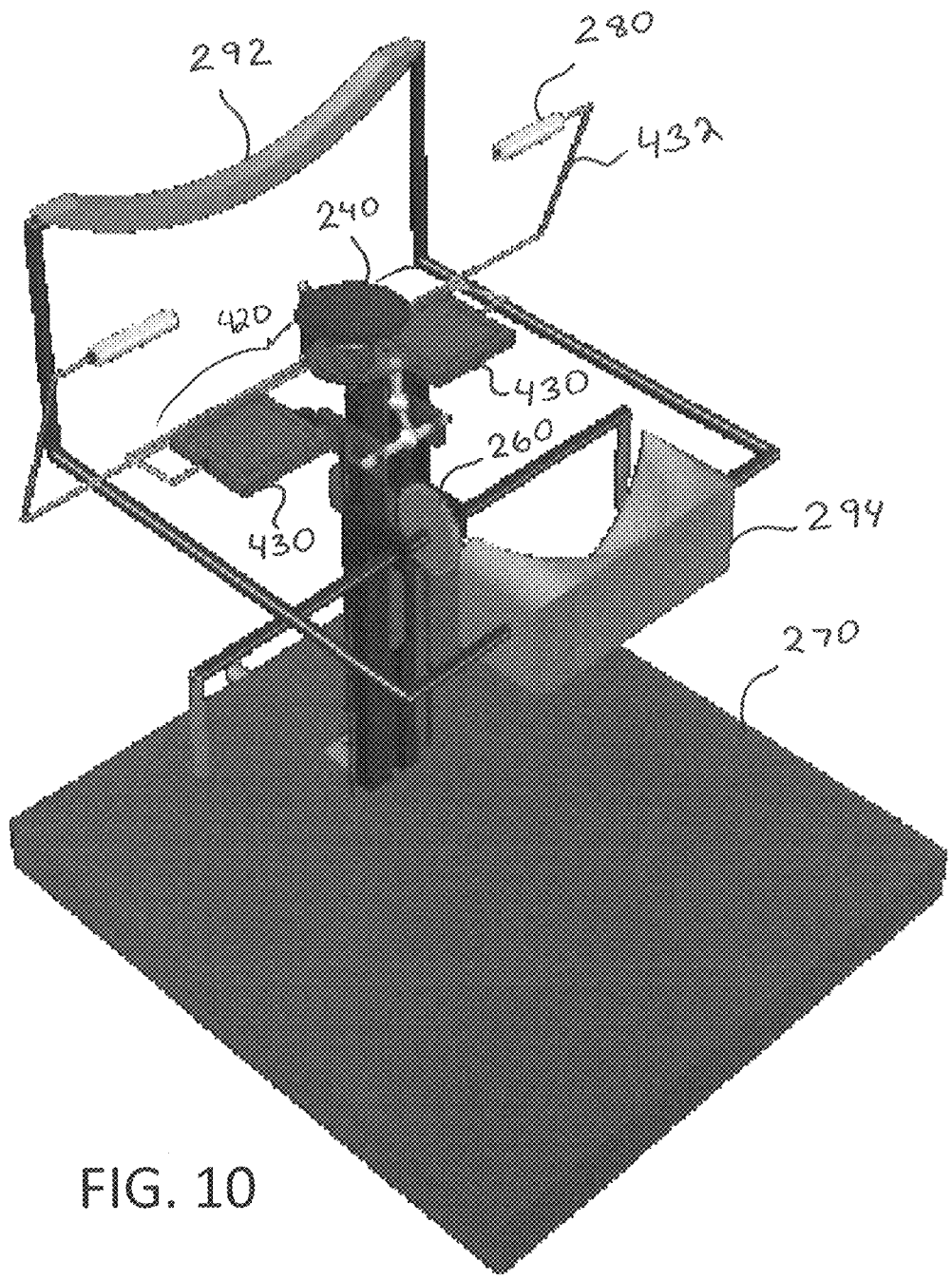
FIG. 10 illustrates an alternative configuration of CLIARA components, this version having dual electronic display screens and a single lens conveyor system.

In one embodiment, the stage is situated in the conduit in a manner that puts the rack 255 on the front side 30 of the tower 250 and the rod and rod sleeve positioned on the backside 35 of the tower, which is illustrated, by way of example, in FIGS. 3 and 8. This configuration of the rack and rod and sleeve could be reversed as well. In an alternative embodiment, the rack 255 is disposed entirely within the conduit and the pinion reaches into the conduit to contact and move the rack. An example of this alternative configuration is shown in FIGS. 7A and 7B. In yet another alternative embodiment, illustrated by FIGS. 4A and 10, the rack 255 can be incorporated as part of the rod sleeve 204. With this embodiment, the pinion contacts teeth on the rod sleeve, similarly to a rack. When turned, the pinion causes the rod sleeve to be raised or lowered, as seen in FIG. 10. This embodiment can eliminate the need for a stage. FIG. 9 shows yet another embodiment, wherein the rack is not only moved by the pinion, but is also slidably secured to the pinion, eliminating the need for a conduit.

It can be seen that there are a myriad of linear actuator mechanism 201 configurations by which a rack and pinion can be engaged with a rod sleeve to facilitate proximal and distal movement of the rod. It is also within the skill of a person trained in the art to determine alternative actuator mechanisms, devices, and methods by which the rod sleeve and rod can be actuated in a proximal/distal direction. Thus, it should be understood that the mechanisms and methods by which the rod sleeve are moved can vary, as long as such variations provide the same function and substantially the same result. Those variations are within the scope of this invention.

It was mentioned above that it can be helpful for the user to have direct control over the operation of the CLIARA 10. This can provide a user with a feeling of safety and can reduce the anxiety that many people feel when inserting or removing contact lenses. User control of a CLIARA can be by direct manual manipulation of the moving elements of the device, for example, by providing control over a rack and pinion embodiment described above. One or more operations of a CLIARA can also be motorized and user control can be by means of various known methods, e.g., switches, knobs, buttons, voice activation, foot pedal controls, etc., that direct the operation of motorized elements. By way of non-limiting example, movement of the rod, rod sleeve, and lens manipulator could be controlled by other types of motorized actuator mechanisms 201, such as pistons, pulleys, joints, hydraulics, screws, etc. By way of another non-limiting example, one or more components of the display system 400 could be motorized. Any of these motorized actuator mechanisms can be controlled by voice command. Alternatively, there can be an additional foot control mechanism by which a user can control one or more actions of a CLIARA and/or components thereof. It is within the skill of a person trained in the art to devise any of a variety of techniques and devices by which one or more components of a CLIARA system can be motorized. It is also within the skill of a person trained in the art to determine an appropriate method by which such motorized actions can be controlled by a user. Such variations are within the scope of this invention.

Figure 18:
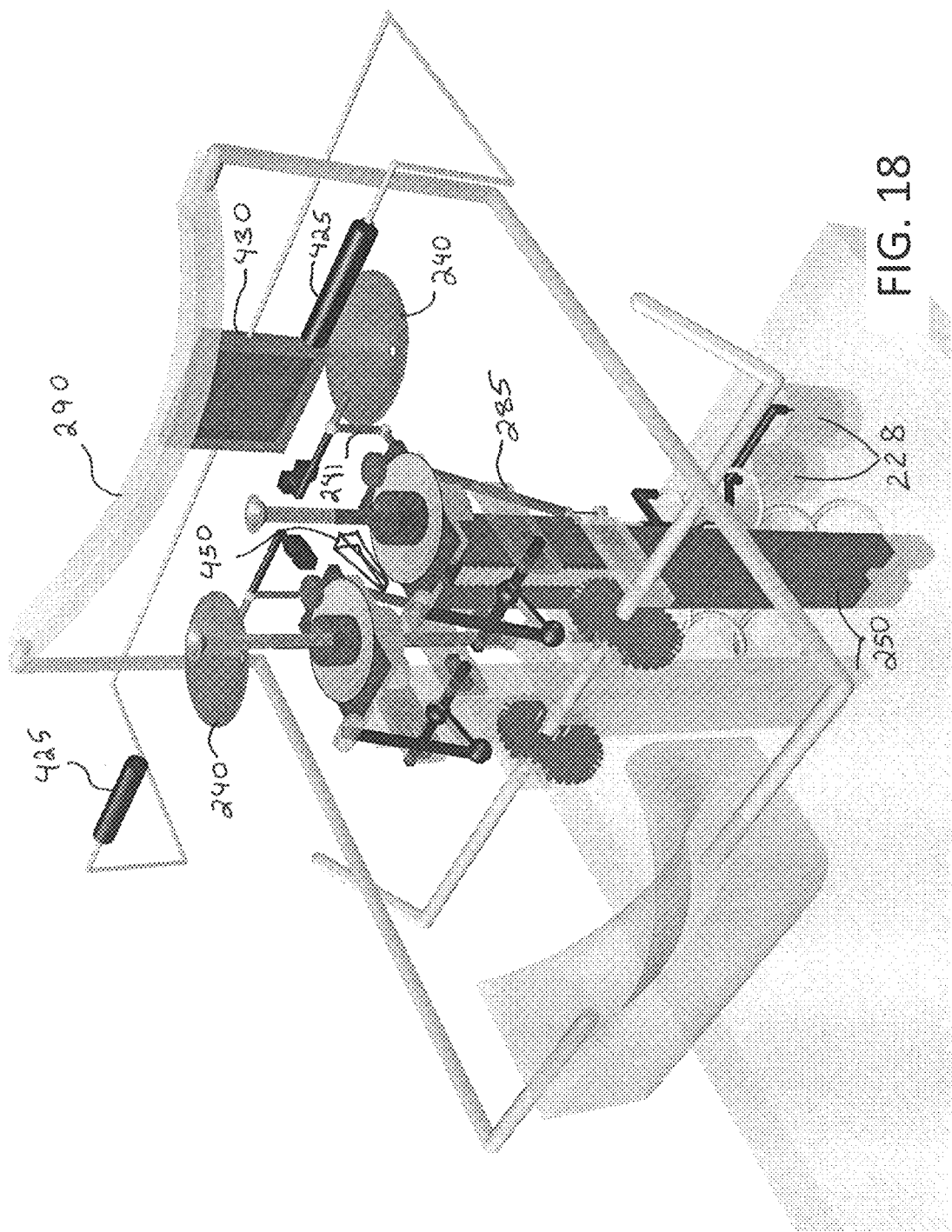
FIG. 18 is an illustration of a different view of the embodiment in FIG. 17, additionally showing the placement of a secondary viewing device comprising a prism.

In one embodiment, a handle 280 is attached to the pinion 260. The handle can be used to manually turn the pinion and raise or lower the rack 255. As mentioned above, the pinion can be fixedly attached to the tower, so that it remains in place, while it turns. FIGS. 1, 8, and 18 show embodiments where the handle is used to hold the pinion in place and the handle is rotatably secured to the support tower 250 with brackets 285, or similar devices. Turning the handle will turn the pinion. Alternative embodiments, which are not shown, but which are within the skill of a person trained in the art, could have a pinion held in place by brackets, or other means, and a handle that operates solely to turn the pinion. In the simplest iteration, the pinion is secured to the tower in a way that allows a user to turn the pinion by directly contacting it with a finger or thumb. In other embodiments, one or more additional gears, joints, actuators, etc. can be operably connected between the user control mechanism, e.g., handle, and the pinion.

It is within the skill of a person trained in the art to determine any of a variety of devices and techniques by which embodiments of a CLIARA could be motorized or otherwise automated for non-manual control. Such variations would be too numerous to list here. However, such variations which provide the same function in substantially the same way with substantially the same result are within the scope of this invention.

In order that the lens manipulator 230 advance the cup 232 portion to the appropriate position for insertion or removal of a contact lens, it is important that the respective eye be in the correct position and orientation. Proper positioning can inhibit undesirable, uncomfortable, or ineffective operation of the cup. As mentioned above, one or more guides 210 can be used to aid a user in proper positioning of the head, face, and/or eye(s). A user can hold their head in the proper position while the cup inserts or removes a contact from an eye. However, it can be helpful, though not required, to have one or more props against which some portion of the face or head can be placed to better ensure that the eye(s) are in the proper position and to reduce random movement that could impede the insertion or removal process.

In one embodiment, one or more props 290 are incorporated with the CLIARA 10 to hold a user's head in the proper position and inhibit undesirable movement. A prop can include any one or more devices or accessories against which the head, face, neck, or upper body can be placed. It can be padded or have some ergonomic shape that aids in placement or comfort. A prop can also be adjustable to a particular user and/or lockable to maintain a preferred position. There can also be visual or tactile indicators to aid in proper placement. In an ideal arrangement, the one or more props will hold the user's head in a position with the face directed substantially downward. This provides the advantageous ability for the lens manipulator to advance towards the eye in a substantially vertical direction to prevent loss of fluid that may be in the vault 17 of a contact lens 15.

Figure 12:
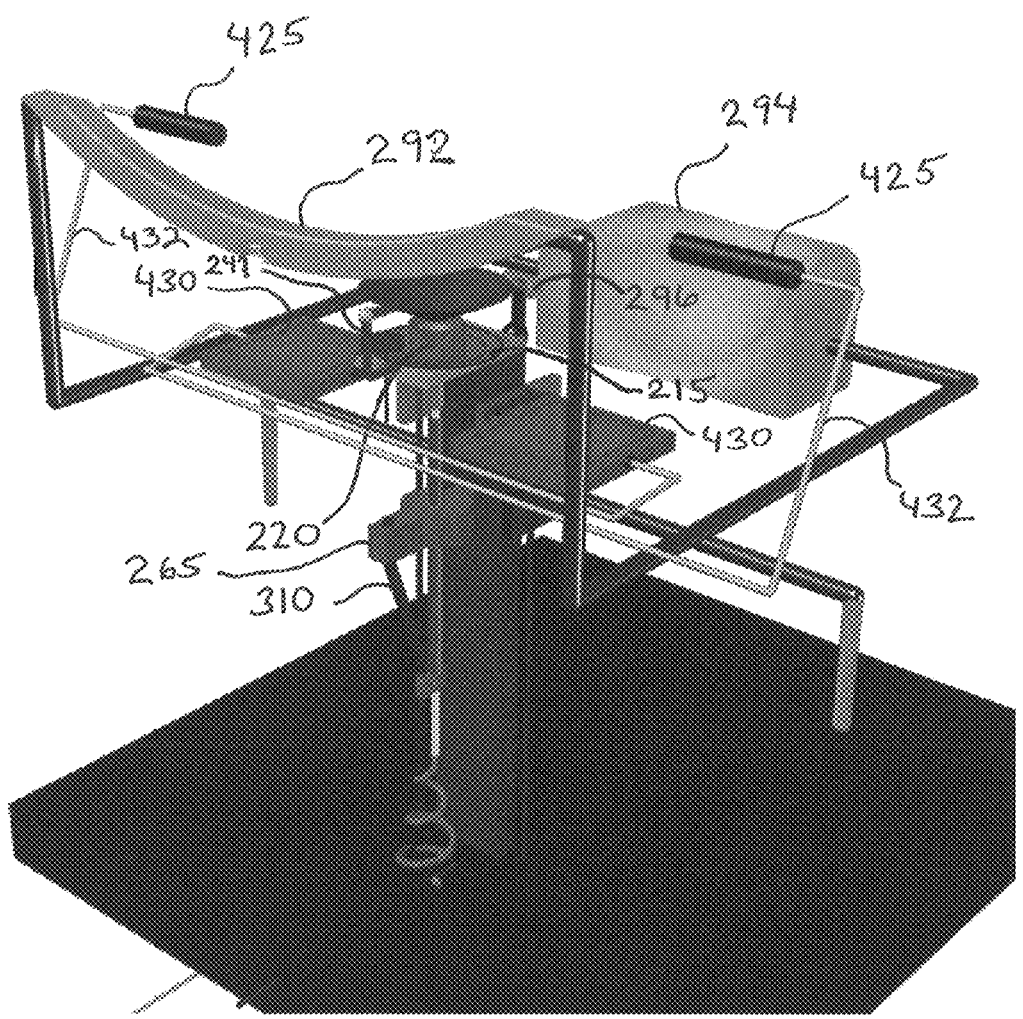
FIG. 12 illustrates another view of the CLIARA shown in FIG. 10.
Figure 13:
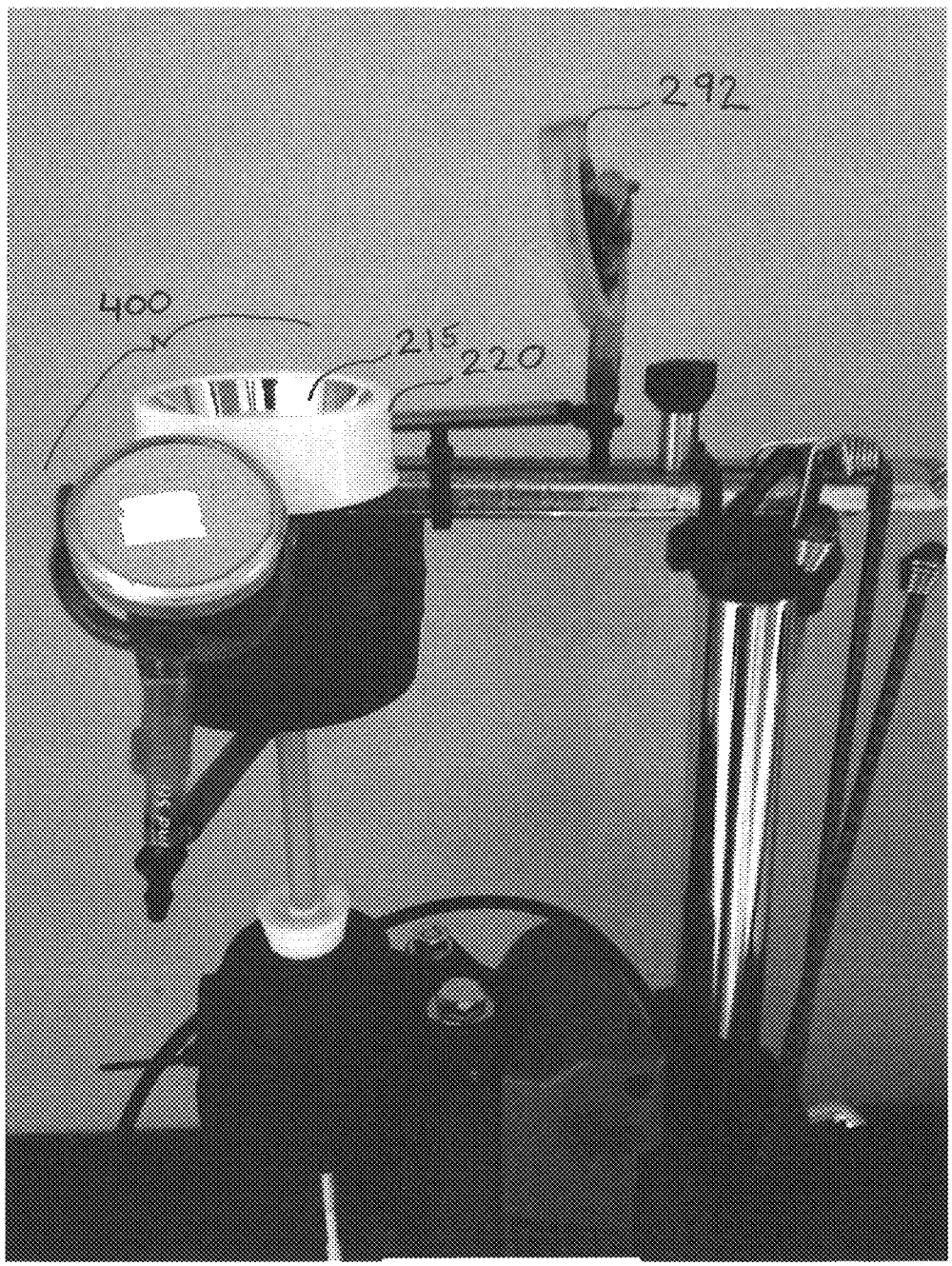
FIG. 13 is a photograph of an enlarged view taken from the side of the lens sink of the embodiment shown in FIG. 9, showing the position of a side-mirror.

In a particular embodiment, shown by way of example in FIGS. 12, 13, and 14, a forehead prop 292 can be located on the CLIARA. In a further particular embodiment, a chin prop 294 can be located on the CLIARA, as also shown in FIGS. 12, 13, and 14. Alternatively, either a forehead prop or chin prop can be used. Thus, the forehead prop and chin prop can be used independently on a CLIARA. But, for certain users, when present on a CLIARA and used together, a forehead prop and chin prop can more easily ensure that the user's head is held at the proper angle during an entire procedure.

Usually, when contact lenses are inserted, it is necessary for one or both of the eyelids to be pulled back from the eye, to provide more eye surface for attachment. Once the head is properly placed on a CLIARA, using one or more props, if desired, the fingers can be used to open the eye lids. However, one or more props 290 can also be used to assist in this procedure. In one embodiment, at least one face prop 296 is located on the CLIARA 10. A face prop can be positioned so that it can assist with pulling an eyelid away from the cornea. FIGS. 6A-6C illustrate an example of a face prop located on a CLIARA near the lower eye area and being used to pull the lower eyelid away from the eye.

With this embodiment, the head can be positioned on one or both of a forehead or chin prop. A face prop can simultaneously make contact with an area near the eye, preferably below the eye socket. The head can then be adjusted slightly forward or backwards on the other props so that the face prop pulls the eye lid in the correct direction away from the eye. Alternatively, the face prop can be adjustable or movable. In one embodiment, the face prop is configured to be moveable or otherwise adjustable, such as by sliding or rotating towards the front side 30 or backside 35. The face prop can be positioned so that it contacts the face near the eye. After the head is positioned on one or both of the forehead or chin props, the face prop can be moved in a direction that causes it to pull an eye lid away from the eye. In a specific embodiment, the face prop contacts the tissue over the zygomatic bone on one side of the nose and below the eye socket. When moved, the face prop can pull the lower eyelid away from the eye. If necessary, fingers can be used to also move the upper or lower eye lid away from the eye. In a further embodiment, a face prop can be lockable, so that it can stay in a position that holds the eye lid away from the eye.

Once the head and face are in position, and one or both eyelids are pulled back from the eye, the eyeball itself should be aligned correctly to receive the contact lens over the cornea. One or more guides on the CLIARA can be used as visual cues that the eye can look at to ensure that it is in the correct position. In a specific embodiment, the rod 202 on which the lens manipulator is positioned can be lighted at the proximal end, by the various methods discussed above. In an ideal embodiment, the rod extending into the channel 236 in the lens manipulator has a visible light at the proximal end, so that a user having their face positioned on one or more props 290 can see and use the light to ensure that the cornea is presented properly to receive a contact lens. In a specific embodiment, by staring directly at the light, the eye will be properly aligned for the cup 232 to insert a contact lens. In a further specific embodiment, a user can avert their eye away from the light, such as towards the nose, to present the cornea and contact lens thereon in an eccentric position relative to the cup, which can be more conducive to removing a contact lens with the cup.

In order for the cup 232 to insert a contact lens, the contact lens must be placed on the proximal end of the cup, as shown, by way of example, in FIG. 6A. This can be accomplished by placing the contact lens directly on the end of the cup with the convex side towards the cup. Various devices can also be used to facilitate placement of the lens on the cup. Insertion of a contact lens is often made easier and more comfortable if the correct amount of contact lens fluid is contained in the lens vault 17. This can be accomplished in several ways, not the least of which is just to drop contact lens fluid onto the contact lens once it is placed on the cup.

In one embodiment, a CLIARA includes a lens sink 220. A lens sink can be used to receive a contact lens and align it over a cup. FIGS. 3, 4A, 12, 14, 22, 23A and 23B show different embodiments of a lens sink 220 that can be used with the CLIARA embodiments of the subject invention. A lens sink is, in general, a receptacle with an interior 222 and a port 224 therethrough. In a specific embodiment, the port is centralized at the bottom of the lens sink. Alternative embodiments can have a port that is not centralized.

In one embodiment, the lens manipulator 230 and rod sleeve 204 pass through the port. More particularly, the tube end of the lens manipulator and rod sleeve pass through the port. This embodiment allows the cup to be located at or near to the proximal end 20 of the port, as illustrated by way of example in FIG. 4A. The tube end 234 of the lens manipulator can protrude through to the distal end of the port and attach to the proximal end of the rod, as explained above. The interior can be bowl-shaped or otherwise at least partially interdigitated with the shape of the cup 232. Ideally, the curvature of the interior 222 is at least partly complimentary to the shape of a contact lens, in particular to a peripheral portion of a contact lens. When the contact lens is placed in the lens sink and situated over the cup, the edges of the contact lens can be against the complimentary shaped portion of the interior 222 of the lens sink. When contact lens fluid is placed into the lens sink, the complimentary shape between the lens periphery and the lens sink interior will facilitate the fluid draining into the lens vault 17 of the contact lens 15. This interior 222 can also assist in aligning the contact lens on the cup, so that it can be accurately deposited onto an eye.

During the process of inserting a contact lens, the lens manipulator and rod sleeve will pass through the port 224. The cup portion will remain proximal to the port, such that is does not enter the port. The cup can pick up the contact lens and transport it to the eye, which is described above. The diameter and shape of the port should, therefore, allow the lens manipulator and rod sleeve to pass through with minimal resistance. The cup can be restricted from entering the port. However, as fluid can also be introduced into the bowl-like interior, which is contiguous with the port, it can be beneficial if excess fluid does not drain through the port.

In one embodiment, the diameter of the port creates a friction fit with the lens manipulator and rod sleeve. The friction fit can prevent fluid from draining into the port as the lens manipulator and rod sleeve traverse the conduit. In a specific embodiment, the material of the port and the material of the lens manipulator and/or rod sleeve can encourage a friction fit that does not inhibit movement through the port, yet still inhibits drainage of fluid. As will be discussed in more detail below, the lens manipulator can be removed from the proximal end of the rod during removal of a contact lens, as part of a safety feature of the CLIARA. Thus, in certain embodiments, it is imperative that the lens manipulator have sufficient friction fit with the port to inhibit fluid flow, but not so much that it requires excessive or dangerous force to remove it from the rod. This could entail using one or more flexible or elastic materials, or materials with a high static coefficient. It is within the skill of a person trained in the art to determine materials suitable for forming an adequate fit between the port, rod sleeve, and/or lens manipulator that inhibits fluid flow. Such variations are within the scope of this invention. Excess fluid can be wiped out of or otherwise removed from the bowl-shaped interior prior to the cup being returned to the lens sink.

Figure 22:
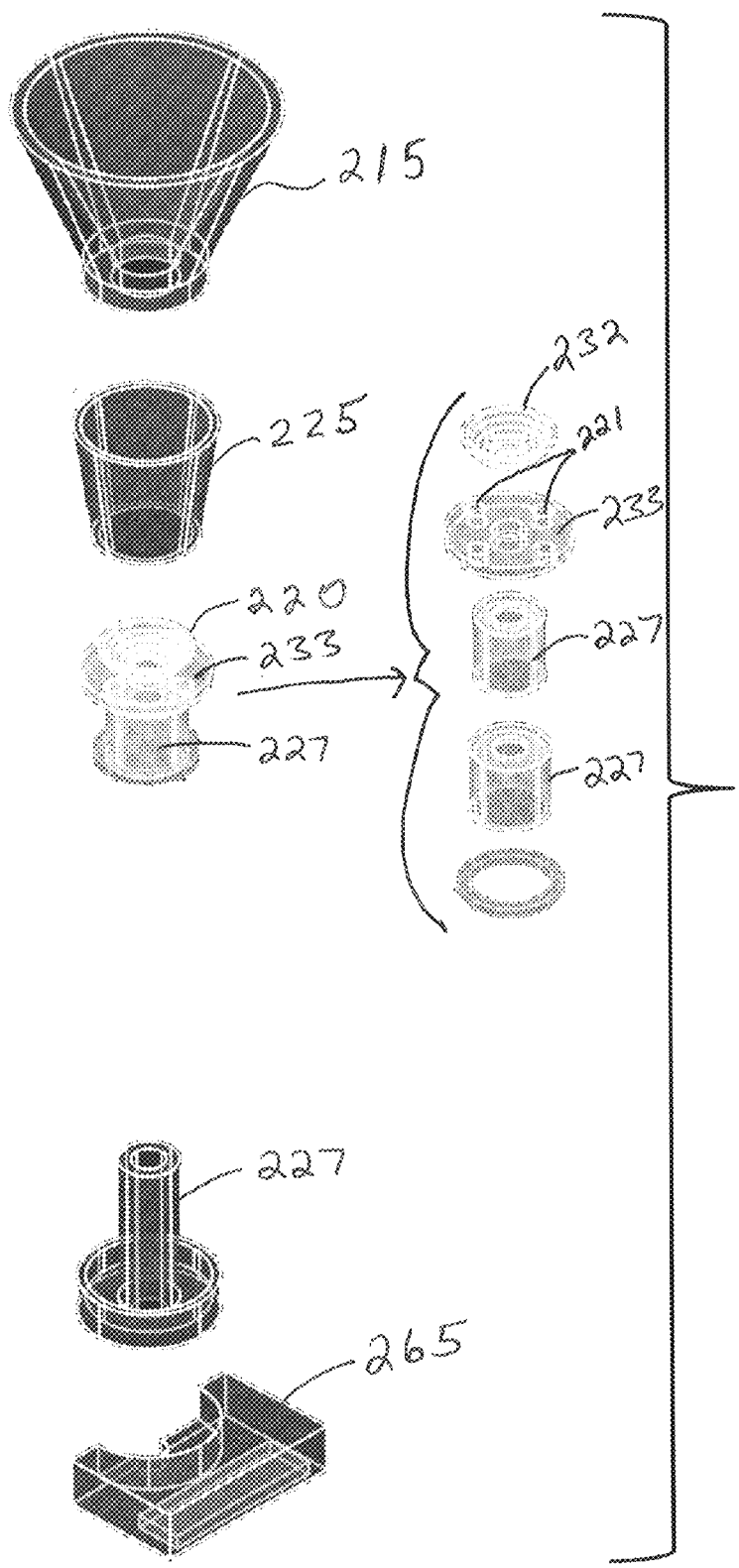
FIG. 22 is an exploded view of some of the components that can be utilized in embodiments of the lens conveyor system of the subject invention.
Figure 23A:
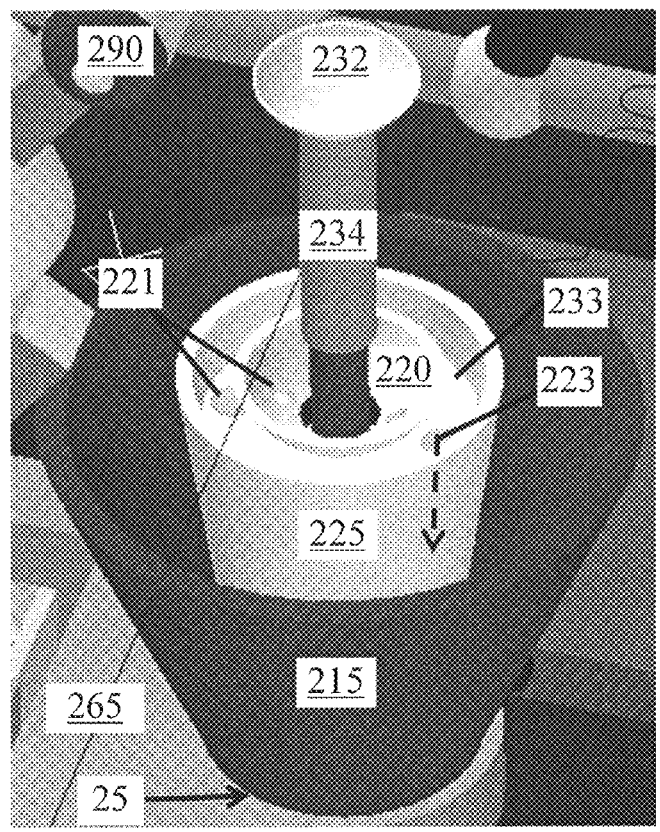
FIGS. 23A and 23B are enlarged views of an embodiment of a lens conveyor system having an alternative embodiment of lens sink that includes drainage holes.
Figure 23B:
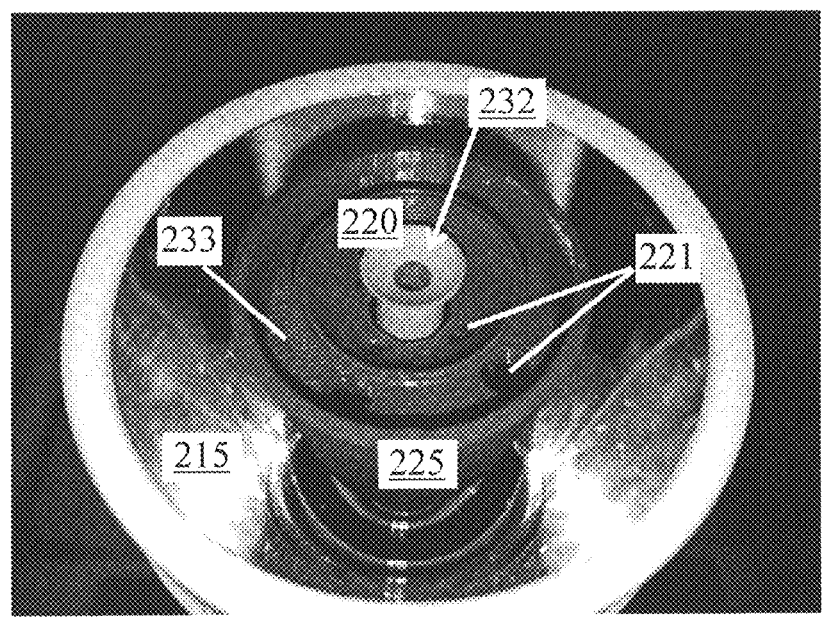

In an alternative embodiment, the port or an area of the channel 236 near the port has one or more diaphragms 226 therein that push or rub against the rod sleeve and lens manipulator sufficiently to seal any space around the rod sleeve and inhibit passage of fluid. The amount of force exerted by a diaphragm on a rod sleeve can depend upon any of several factors understood by those with skill in the art, including, but not limited to, the materials utilized for the port, rod sleeve, and/or lens manipulator; the viscosity of the fluid; the diameter of the port; the length of the port; and other factors. A diaphragm can be a flexible shoulder, lip, or just a thin piece of flexible material protruding from the port wall to the interior of the port, as shown in FIG. 4A. As the tube end 234 of the lens manipulator and/or the rod sleeve passes through the port, the diaphragm rubs against or pushes against these components to form a seal that inhibits fluid from passing through. A diaphragm can be flexible so that it can bend or flex as necessary to form a seal as the tube end and rod sleeve pass in either direction. Alternatively, a diaphragm can be rigid with an edge that contacts the lens manipulator and rod sleeve. The point is that the diaphragm can inhibit fluid from draining, or at least easily draining, into the port, but does not undesirably inhibit the lens manipulator from being removed from the rod. The shape and number of diaphragms can vary depending upon a variety of factors understood by a person skilled in the art. Such variations which perform the same function in substantially the same way with substantially the same results, are within the scope of this invention. In yet another embodiment, the lens sink 220 can be configured with one or more drain holes 221 that allow fluid from the lens sink to drain into an overflow cup. FIGS. 22, 23A and 23B illustrate an embodiment of a lens sink having drain holes that lead to an overflow up 225 positioned below the lens sink. The overflow cup can be configured to go at least partially around the port 224, where the rod sleeve 204 reciprocates, so that fluid is inhibited from draining into the port. FIG. 22 illustrates one example of this where the overflow cup includes an inner sleeve 227 that can be contiguous with the container, so as to create a storage space 223 between the sleeve and the overflow cup into which the fluid can drain. There can be one or more additional sleeves, which can be coaxial with the rod sleeve. These additional sleeves can aid in reciprocation of the rod sleeve within the channel 236 and the port 224, or provide support for the overflow cup or for other sleeves on the stage 265, or provide further storage spaces for storing excess fluid received through the drain holes, or have other uses that would be understood by a person skilled in the art.

To ensure that the fluid that drains from the drain holes in the lens sink further drains into the storage space, there can be divider 233 positioned within the overflow cup, distal 225 to the lens sink, and proximal to one or more sleeves, as shown, for example in FIGS. 22, 23A, and 23B. The divider can further define the storage space for containing excess fluid can have one or more drain holes that lead into the storage space, as shown in the example in FIG. 23A.

Ideally, one or more of the overflow cup, one or more sleeves, the divider, the rod sleeve, other components or some combination thereof can be removed from the CLIARA. This can permit decanting of the collected fluid and cleaning and/or sterilization of the removed components. One or more of the components can also be disposable and/or replaceable, such that cleaning or sterilizing is unnecessary or at least not required. Alternatively, excess fluid can be removed by other techniques and devices known in the art and the overflow cup and other components related thereto can be cleaned while still installed on a CLIARA.

Depositing contact lens 15 fluid into the lens vault 17 or the lens sink can often be accomplished by using a fluid storage bottle, which is often configured to deposit fluid in droplet form. Typically, the end of the bottle can be placed over the lens sink and or contact lens and individual drops can be expressed from the opening. However, for some users this may not be a feasible option. To aid users who may not be able to express drops accurately into the lens vault 17 or lens sink, a funnel 240 can be used. In one embodiment, a rotating arm 241 is affixed to a funnel and to the CLIARA. When it is desired to place drops into the lens vault or lens sink, the funnel can be rotated to the correct position over the lens sink or contact lens which has been placed on a cup 232. Once the fluid has been deposited, the funnel can be rotated away from the contact lens or lens sink. FIGS. 2 and 12 illustrate embodiments of a funnel rotated over a lens sink.

FIGS. 7B and 10 illustrate an embodiment where the funnel has been rotated away from a lens sink so that the lens conveyor system 200 can operate.

The process of removing a RGP contact lens from the surface of an eye using a CLIARA of the subject invention is similar to the process of inserting a contact lens. The head and eye can be aligned with the lens manipulator, using one or more props 290 if available. The lens manipulator can be advanced by the rod towards the eye, as described above, to attach to a RGP contact lens. Prior to the cup 232 on the lens manipulator 230 reaching the contact lens, the eye should be slightly averted away or should look slightly away from the cup. This will put the cornea and contact lens thereon in an eccentric position that is more conducive for removal. Usually, the eye can be averted towards the nasal area. But, it is also possible, and for some users perhaps preferable, to avert the eye away from the nasal area or even up or down to provide the necessary eccentric angle. The cup can be advanced until it makes contact with an off-center position of the contact lens to create a suction force with the contact lens. Once the cup and contact lens are connected, the lens manipulator can be retracted by moving it downward and away from the eye. The eccentric angle of the lens will cause it to be peeled off or raised off of the cornea, whereby one side is lifted off the cornea first and the contact lens is then incrementally lifted or peeled off.

It can be preferable for an eye specialist to adjust the CLIARA for removal of a contact lens. An eye specialist can adjust how far the lens manipulator advances, the amount of suction that is formed with the contact lens, and can also provide instructions for averting the eye to a correct angle, and provide other calibration or information. However, even with professional calibration and proper operation, the CLIARA may not be capable of removing a contact lens. It is not unusual for a contact lens to form an adherence with the cornea that is stronger than usual. This is often caused when the eye becomes too dry, which causes decreased pressure between the contact lens and the cornea and conversely increases the suction force between them. It can also occur due to normal changes in the eye while wearing a contact lens. The shape of the eye can be temporarily changed, which might increase adherence. It is also possible that the eye might not be sufficiently averted nasally when the cup makes contact, which can make it more difficult to lift the edge to peel off the contact.

If during the process of removing a contact lens it is determined that the cup 232 will be unable to remove the contact lens from the surface of the eye, the cup 232 on the lens manipulator 230 will need to be disengaged from the contact lens. As mentioned above, the rod being disposed within the channel 236 in the tube end 234 can be used to adjust the amount of suction force that a cup can achieve. This arrangement also allows for the suction force to be completely negated by removing the rod from the tube end or pulling it out sufficiently that air can ingress into the channel, reducing or eliminating the suction force behind the cup. In one embodiment, the lens manipulator 230 can be removed from the rod by moving the head away from the lens manipulator. The fingers can be used to temporarily stabilize the lens manipulator on the eye, as the head and eye are moved away from the lens manipulator. As the head and eye move away from the lens manipulator, the suction force between the contact lens and the cup will initially keep the cup attached to the contact lens. But, as the head and eye continue to pull the tube end 234 of the lens manipulator 230 from the rod, ambient air will force its way into the channel. When sufficient air is in the channel, and it usually will not require a large amount, the suction force created between the cup 232 and the contact lens will be released. In a specific embodiment, the lens manipulator 230 and the proximal end 20 of the rod can be shaped, such as, for example, with a taper or cone shape, that permits air into the channel without the rod having to be completely removed from the tube end. The rod could also be configured with various cut-outs, divots, depressions, or even openings, pores, holes, or channels that can be exposed when the rod is pulled from the channel. Such openings can allow air into the channel more quickly without having to remove the rod very far in the channel.

Figure 16:
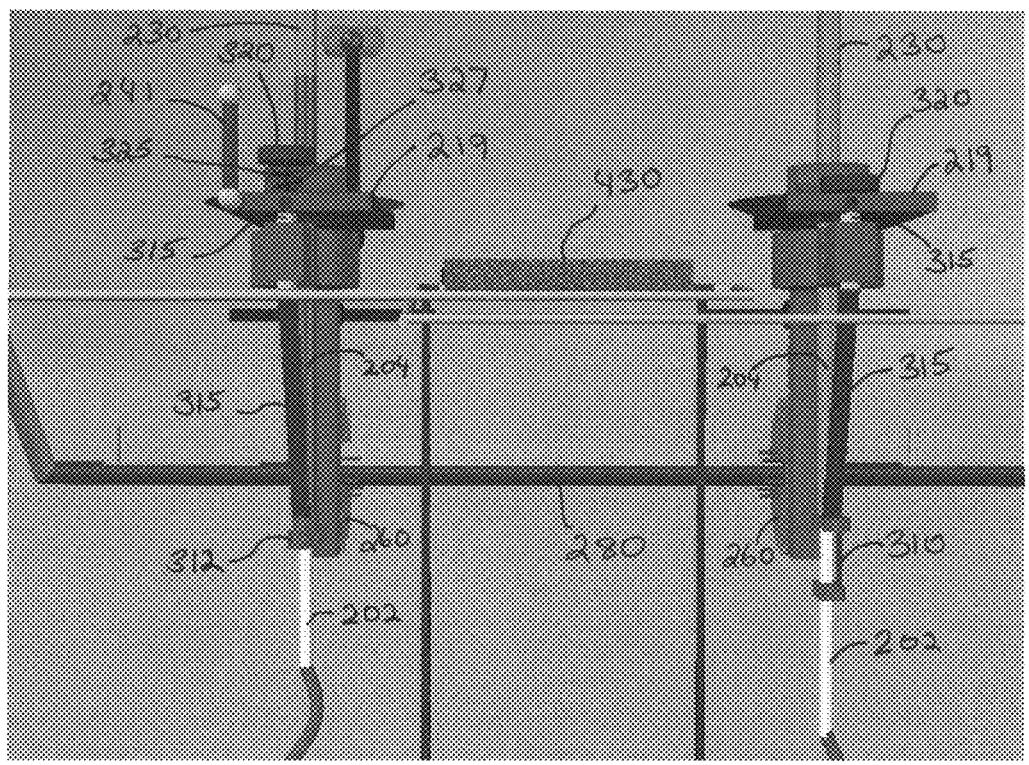
FIG. 16 is an illustration from the front side showing an enlarged view of a CLIARA with a dual lens conveyor system.

Alternatively, an emergency release system 300 can be utilized to remove the rod from the lens manipulator without moving the head or eye. An emergency release system can be used to disengage a rod from the tube end 234 and channel 236 of the lens manipulator. More specifically, an emergency release system can be at least attached to the rod and can be used to pull the rod away from the lens manipulator 230, extracting it from the tube end 234. FIGS. 2, 8, and 16 illustrate non-limiting examples of emergency release systems.

In one embodiment, an emergency release system 300 includes an actuator apparatus 310, such as, for example, a linear actuator apparatus, that is connected to the rod at one end and a controller 320 at the other end. A controller can include, but is not limited to, levers, buttons, switches, knobs, pulls, or other types of mechanisms, that act as linear actuators, or can rotate, turn, flip, slide, or some combination thereof to move the linear actuator in a desired direction. An actuator apparatus can be any of numerous devices capable of exerting a force on the rod so as to pull the rod out of the channel. Typically, a linear actuator apparatus is a rigid or semi-rigid object that can be pushed or pulled to exert a force.

In a particular embodiment, shown for example in FIGS. 8 and 16, a linear actuator apparatus is a semi-rigid cable that can be moved between the controller 320 and the rod 202 where it extends from the distal end 25 of the rod sleeve 204. The linear actuator apparatus can be fixedly attached to the rod by any operable method or device known in the art. It can be joined directly to the rod or with any of a number of known coupling devices. In one embodiment, a clamp 312 is used to operably connect the distal end 25 of the linear actuator apparatus 310 to a part of the rod 202, which extends out of the distal end of the rod sleeve 204.

In a further embodiment, a guide sleeve 315 can be used to support or guide the cable. The cable and guide sleeve can be attached, such as, for example, like throttle cables that are known in the art. Alternatively, the cable can be within the guide sleeve, but not attached, or only partially attached, to the guide sleeve. Thus, the guide sleeve might only be used more to ensure the proper direction of movement of a cable. A guide sleeve can also be any length or diameter. In a specific embodiment, shown in FIGS. 2, 8, and 16, the guide sleeve extends through the rod sleeve stage 265, such that it is moved proximally along with the stage and the linear actuator. Other types or configurations of guide sleeves can be incorporated with the embodiments of the subject invention. Such variations are within the scope of this invention.

In most circumstances, the emergency release system 300 can only be activated after the rod sleeve stage has been raised, so as to raise the lens manipulator to the eye. In a specific embodiment, the linear actuator apparatus goes through the rod sleeve stage, as shown, for example, in FIGS. 8 and 16. When the rod sleeve stage is advanced proximally, as described above, it carries the proximal end of the linear actuator apparatus into proximity of the controller 320. The controller and linear actuator can be unconnected. Alternatively, the linear actuator apparatus and controller can be connected and the controller can be moved proximally concurrent with the linear actuator apparatus. FIGS. 8 and 16 illustrate a specific embodiment, where the controller is a button with a pin 325 above the rod sleeve stage 265. In this specific embodiment, the button is shown on a platform 219 supporting a guide mirror and lens sink. However, in other embodiments, such as the one in FIG. 2, the button can be situated through a guide mirror without benefit of a platform. The pin 325 can extend through the platform, guide mirror, or whatever other device is used to support the button so that it can operably connect with the linear actuator apparatus.

FIG. 16 illustrates an embodiment, which will be discussed more below, but which illustrates an example of an actuator apparatus and controller arrangement and their operation. The left side of the device shows a button controller 320 biased to a raised position with a spring 327, which can optionally be used. The pin 325 shown here can moveably extend through a platform 219 and is not connected to the actuator apparatus 310, which is shown here as a linear actuator apparatus. In FIG. 16, the stage and lens manipulator 230 are shown in a raised position, where the proximal end 20 of a linear actuator 310 and a guide sleeve 315 are in proximity with the distal end of the pin 325. The right side of FIG. 16 shows the button controller 320 pushed downward or distally so that the pin contacts the proximal end of the linear actuator 310 within the guide sleeve 315. Upon pushing the button, the linear actuator is forced distally, which in turn, because of the connection, forces the rod to also move distally. With the lens manipulator still in a raised position, as shown in FIG. 16, when the rod moves distally with the linear actuator, it can be pulled out of the channel 236, at least partially or entirely, opening the channel between the pore 231 in the cup and the distal end, eliminating the suction force of the suction cup, as detailed above.

The alignment of the eye with the lens manipulator 230 is important to ensuring that the CLIARA operates properly. Proper alignment can mean having the head and face properly situated and can also mean that the eye is looking in the correct direction or is at the correct angle, as the lens manipulator and cup approach the eye. One advantage of using a CLIARA of the subject invention is that it can eliminate the need to touch the eye with the fingers in order to insert or remove a contact lens. It can also ensure that the only object that touches the cornea of the eye is a contact lens. Ideally, the contact lens has been cleaned, sterilized and is free of debris prior to being inserted. The lens manipulator can ensure that it remains that way during the entire insertion process. However, if the eye is not properly aligned, the cup can insert the contact lens incorrectly, out of position, or may touch other areas around the eye. Likewise, during the removal process, the lens manipulator, as it approaches the eye may contact the cornea or eyelids and not properly attach to the contact lens if the eye is not aligned. Thus, the subject invention can include any of a variety of mechanisms that can be used to ensure that the eye is properly aligned at all times.

In one embodiment, visual indicators are strategically placed on the CLIARA that assist with directing the eye to the correct direction or guide a user into looking in the correct direction. Visual indicators have been mentioned above with respect to the lighted rod, as well as other types of indicators known in the art could be used with embodiments of the CLIARA.

In a particular embodiment, a guide mirror 215 is incorporated with the lens cup. The guide mirror can be used to see other visual indicators 216 on the CLIARA and align them in such a way that in so doing, the eye is properly aligned. In a specific embodiment, the lens manipulator 230 and/or the rod sleeve 204 can have one or a plurality of indicators that are reflected in the guide mirror. A user engaged with the CLIARA, can view the indicators in the mirror and use the mirror to line-up or arrange the guides in a pre-determined manner. This can be done by moving the head for larger corrections and then moving the eye itself to make minor corrections. Once the user sees the indicators 216 in the proper alignment or configuration, they can be assured that the eye is in the proper position for insertion or removal of a contact lens.

A guide mirror can be placed in any of several locations on the CLIARA. In one embodiment, the interior of a lens sink 220 actually comprises a reflective surface that can be a guide mirror 215. FIGS. 11 and 13 show an example of a lens sink with a reflective interior 222 that can be used in conjunction with one or more visual indicators on the CLIARA to align the eye. Visual indicators can be strategically placed so that they are reflected in the lens sink. As long as the visual indicators appear to one or both eyes as being aligned or in the proper position, the cup 232 will make proper contact with the eye and/or contact lens. FIGS. 3, 5, and 10 show examples of elongate visual indicators 216 on a lens manipulator that reflect into a reflective lens sink.

Figure 15A:
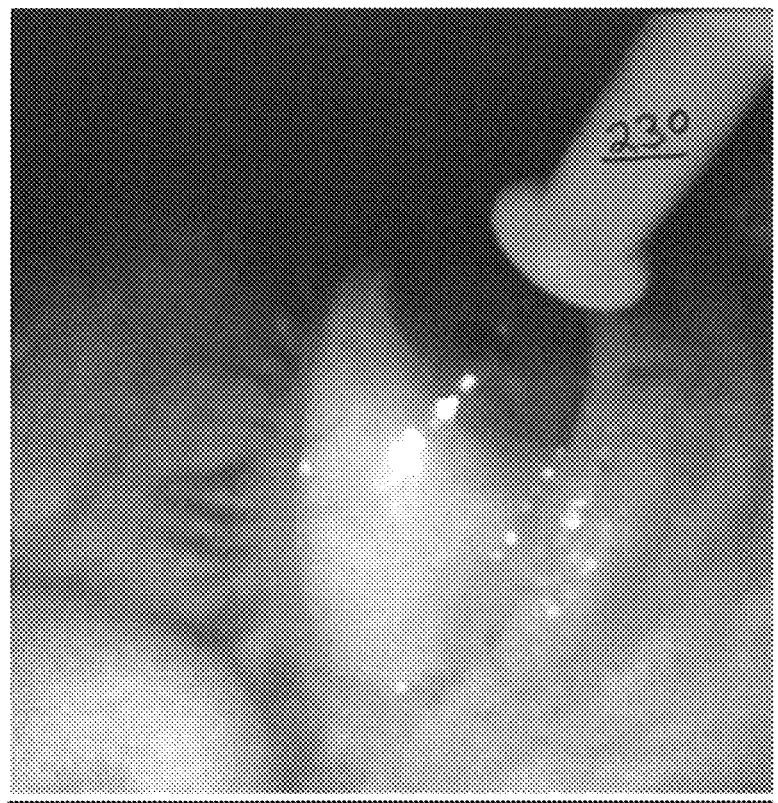
FIGS. 15A-15E illustrate the optical illusion created by the dual image system embodiments of the subject invention.
Figure 15B:
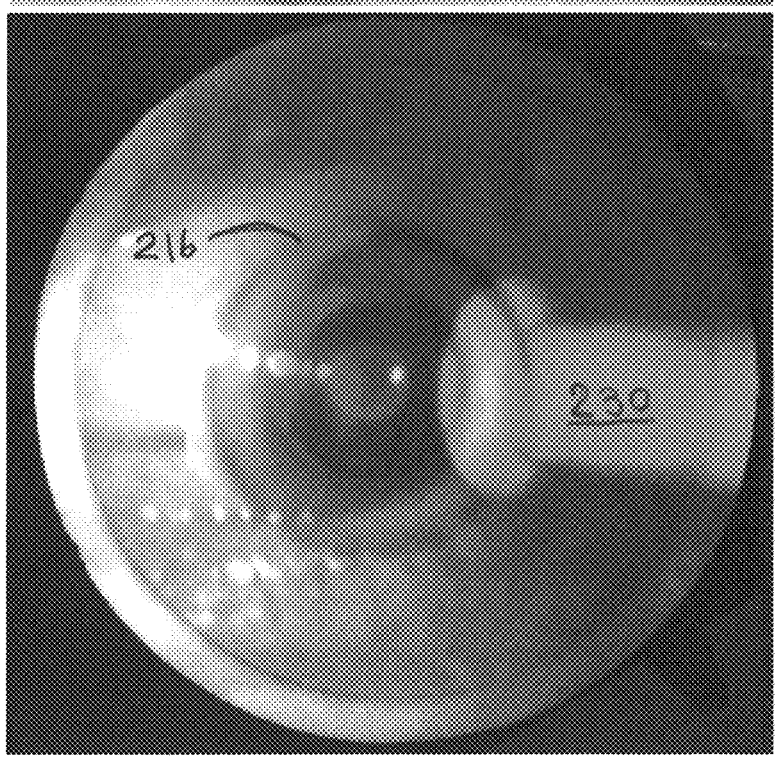

In an alternative embodiment, a guide mirror can be situated around a lens sink. Such a guide mirror can have any desirable shape. In a particular embodiment, illustrated by way of example in FIGS. 2, 4A, and 12, the guide mirror is circular and has a concave surface, which reflects, or has thereon, one or more visual indicators 216. One or more visual indicators can be reflected in a manner that one or both eyes can see to position the eye in the correct direction. Alternatively, visual indicators can be placed directly on the mirror. For example, a series of concentric rings can be placed directly on the mirror surface. A user looking in the direction of the lens manipulator will see their eye or face in the mirror and can use the reflection to align the rings with a portion of the eye. For example, FIG. 15B illustrates an embodiment where a series of concentric rings are reflected back to the user who uses the reflection as an indicator 216 to ensure that the cornea is centered in the middle of the smaller ring. Other embodiments of guide mirrors and visual indicators that could be used with the embodiments of the subject invention are known to those with skill in the art. Such alternatives are within the scope of this invention. The embodiments of the subject application provide a user with the advantageous ability to control the insertion and removal of a contact lens from their eye without use of the hands or fingers making contact with the eyeball itself. If necessary or desired, the fingers can be used in conjunction with embodiments disclosed herein to further open the eyelids. But, specific embodiments disclosed herein can even eliminate the need for that much interaction of a user with the contact lens insertion or removal process. Guide mirrors and visual indicators can also be used to assist in placing the head and eyes in proper alignment or direction for an accurate insertion or removal process. It can be additionally beneficial if an entire process can be seen by a user, to ensure accuracy and increase the sense of security to a user about the process being conducted. For example, as the lens manipulator comes closer to the eye, it becomes more difficult to see the visual indicators and mirrors. If a user can better see or visualize the contact lens making contact with the eye while also being able to see visual indicators or other cues for as long as possible, it can greatly enhance the user's comfort and sense of safety, and can ensure continued use of contact lenses.

One embodiment of the subject invention utilizes a display system 400 that takes advantage of an optical illusion phenomenon that occurs when a user can see the operation of the lens manipulator from at least two different angles. It is well known and understood that when two different images of the same object at a slight angle are seen by each eye, the brain merges them, so that the dual images are perceived to be a single image, usually accompanied by the feel of depth and three dimensions. The advantage of the display system 400 embodiments of the subject invention is that they employ a type of ultra-parallax imagery, which prevents the brain to merge the two images into one, but the images are rather overlaid, so that they are both interpreted independently but simultaneously by the brain. This allows a user to see an entire insertion or removal process from two vantage-points at the same time, as shown in FIG. 15A. The dual imagery system ensures that at least one eye can, at all times, see the actions of the lens manipulator 230 and the location of the contact lens relative to the eye.

Embodiments of the subject invention use a display system with one or more viewing mechanisms 405 that present to a user, engaged with a CLIARA, two different images to each eye. A unique advantage of the CLIARA system is that it provides each eye with two completely different views of the process, with each view being seen from a different angle. These different angles, when presented to the eyes of a user, are mentally combined, overlaid, or melded allowing the user to see the entire process as it happens. This process can be considered a type of parallax viewing, which is defined in the art as a displacement or difference in the apparent position of an object when viewed along two different lines of sight, and is measured by the angle or semi-angle of inclination between those two lines. Parallax occurs naturally in human sight due to the distance between the eyes, and is responsible for the perception of stereopsis. The embodiments of the subject invention utilize an "ultra-parallax" technology where the display system 400 can present an image seen by one eye that has an angle of inclination that is greater than normal binocular vision or greater than normal human parallax, preventing the images from being merged by the brain into a single three dimensional image, and are therefore perceived independently as an overlaid or compound image.

For example, as described above, when a user is engaged with a CLIARA, a first eye can see the interior 235 of the lens cup or the lens sink and the second eye can view an image, as presented by the viewing mechanism 405 of the display system 400, that is out of the line of normal sight of the second eye. This second image can be taken from any angle and displayed to the second eye by the display system. In one embodiment, the second image is a view of the lens manipulator. The view can be taken from any of a variety of angles and is typically taken from an angle that cannot be seen normally with the second eye when a user is engaged with a CLIARA device 10. Such an angle of view is referred to herein as an "ultra-parallax" view, meaning that it is outside of the normal line of sight of the second eye, when a user is engaged with a CLIARA device. This can, but is not required, to be an angle that is substantially orthogonal to the line of sight of the first eye. Still further, the image seen by each eye can be significantly different, such that the brain does not perceive a typical stereoscopic image. A stereoscopic image is often created by presenting each eye with a slightly offset view of the essentially the same picture. This can provide the user with an impression that the images are 3-dimensional (3-D). However, when the images presented to each eye are significantly different, they brain simply overlays or overlaps the images, such that one appears to be on top of the other. But, there is not a stereoscopic effect.

Figure 15C:
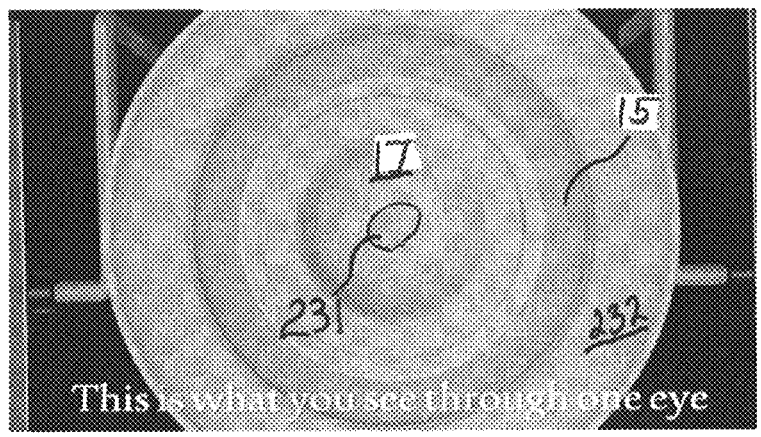
Figure 15D:
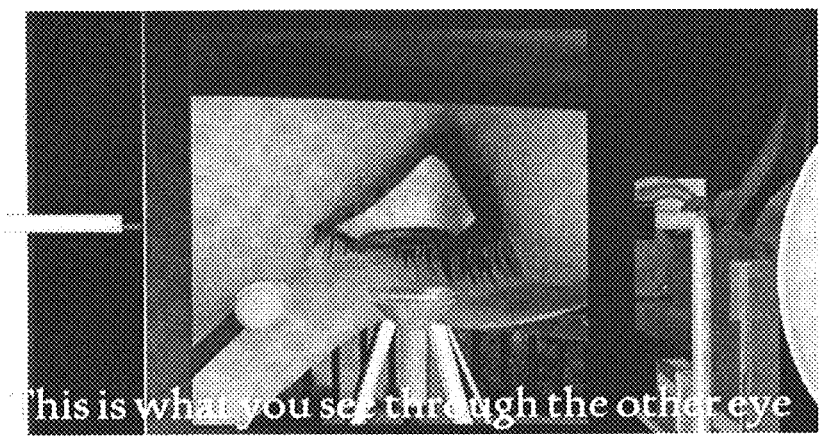
Figure 15E:
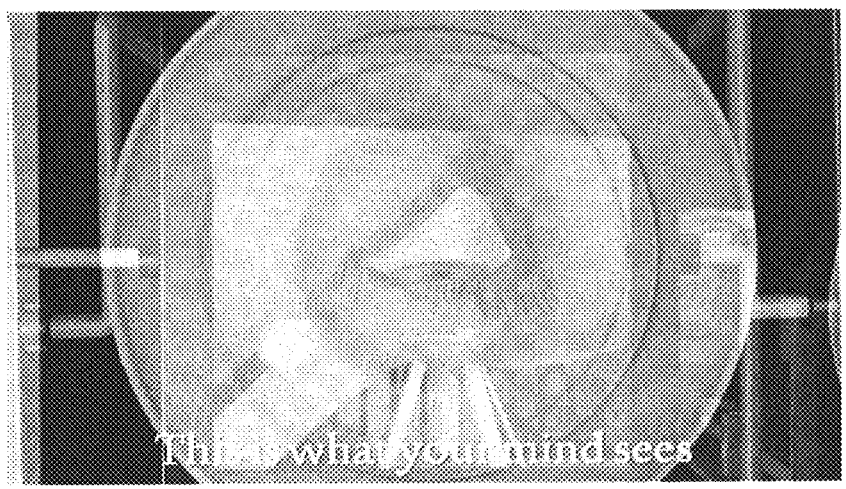

In one embodiment of the subject invention, the first eye can see the lens manipulator and, more particularly, the concave interior 235 of the cup and/or the lens vault 17 as it moves up and down on the rod (see FIG. 15C) and the second eye can see an image taken or acquired by the display system and shown on a viewing mechanism, of the lens manipulator taken from a different angle than that seen by the first eye. For example, the second eye can be shown a side, or a substantially orthogonal, view of the lens manipulator. This second image can also show the lens manipulator and cup as it rises and comes towards the first eye, (see FIG. 15D). The image seen in the second eye can further be that taken from the opposite side of the face or head so that the image shows the lens manipulator operating relative to the first eye, such as shown in FIG. 15D. Due to an optical illusion created by this unique type of ultra-parallax imagery, the brain of a user seeing these dual images will automatically combine or overlay them allowing the view of the lens manipulator approaching from a two different vantage points as it approaches the eye (see FIG. 15D). This can allow the user to further see the cup during the entire procedure, as it deposits a contact lens onto the eye, or as it attaches to a lens for removal. This can give a user a sense of greater control over the process, particularly since the user controls the operation of the lens manipulator. FIG. 15A is a photographic image of a lens manipulator as it approaches the eye of a user. FIG. 15B shows a photographic simulation of the mentally-combined image of the process as it can appear to a user when presented with a display system of the subject invention. These figures illustrate an embodiment where the two views presented to the eyes of a user are substantially orthogonal. As mentioned above, it is not required that the views be orthogonal. The angle between the views can be greater than or less than 90°. In fact, it is possible for the views to be taken at any angle, which is conducive to providing the user with an adequate or beneficial view of the installation and/or removal process. As mentioned above, the images presented to each eye are sufficiently different that a 3-D image is not perceived by a user and are not a typical parallax view. Rather, the disparity between the images prevents a true 3-D image and there is more of an overlay or overlapping effect of the images, such that a user can see both images and the movement of both images simultaneously, but not as a 3-D image. A person with skill in the art will be able to determine the appropriate position for the components of a display system, discussed below, to provide a desired viewing angle. Such variations which provide the same function, in substantially the same way, with substantially the same results are within the scope of this invention.

When a user presents to an embodiment of a CLIARA system, they may be wearing contact lenses or, as will be described, the user may be removing contact lenses using a CLIARA system. In either case, there can be a point during use at which the user has impaired eyesight. One or more of the components used with a display system of the subject invention can be configured to be adjustable to the eyesight of a user as it changes during use. Thus, the mirror system 410 or the electronic imagery system 420, described below, can have components that are adjustable to accommodate a user's eye sight, or changes therein, during use. By way of non-limiting example, the mirrors utilized with a mirror system can have an adjustable position, so that they can be moved closer to or further away from a user to accommodate eyesight. By way of another non-limiting example, the one or more screens utilized with an electronic imagery system can have an adjustable position or an image displayed thereon can be adjustable in any of a myriad of ways to improve viewing thereof. There can also be one or more additional accessories, such as magnifying lenses, that can be added to the system to improve or adjust visual acuity during use. A person with skill in the art would be able to determine which one or more components of a display system can be configured to be adjustable. Such variations, which provide the same function, in substantially the same way, with substantially the same result, are within the scope of this invention.

Figure 19:
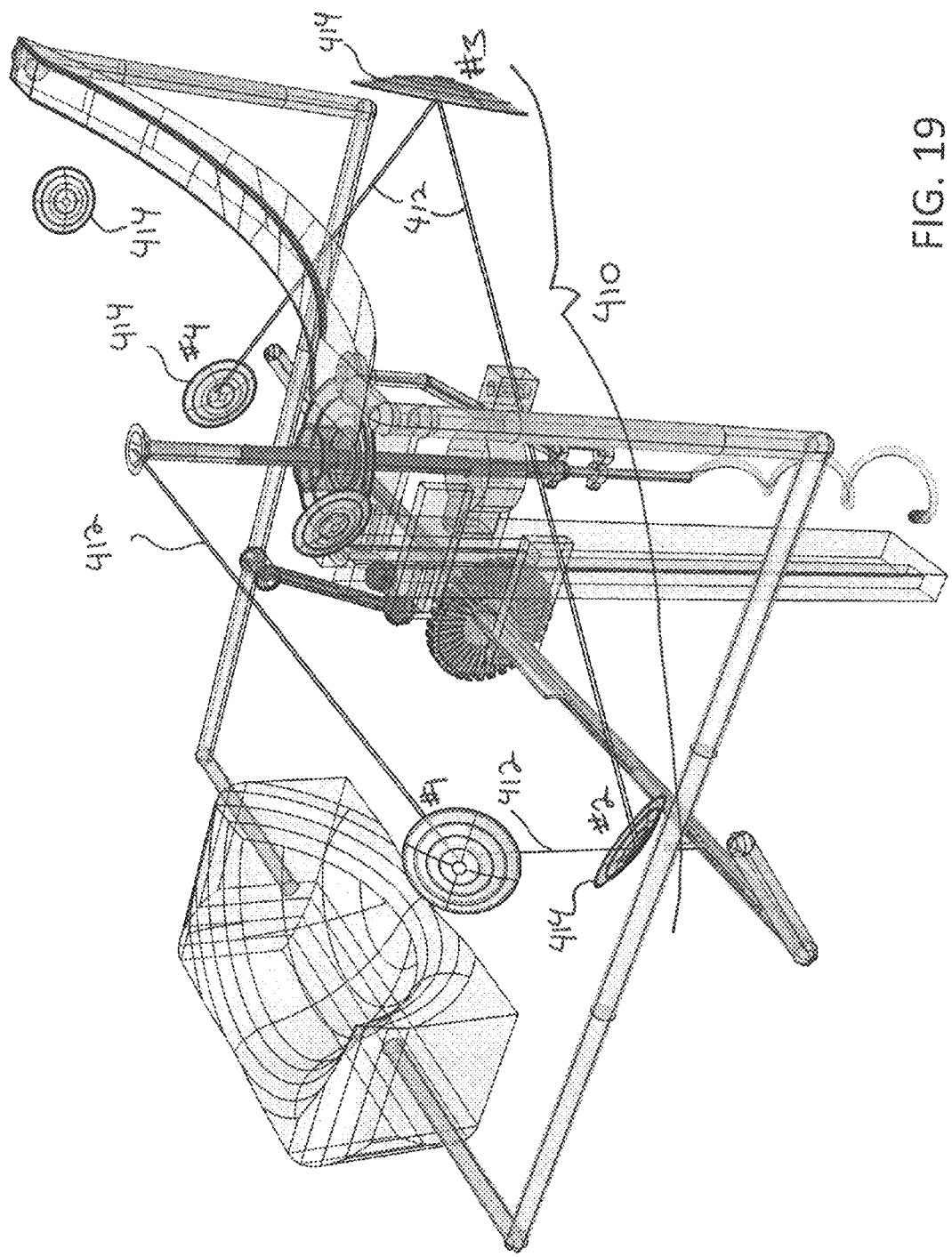
FIG. 19 is an illustration of an alternative embodiment that utilizes multiple mirrors to provide a view of the insertion process.
Figure 20:
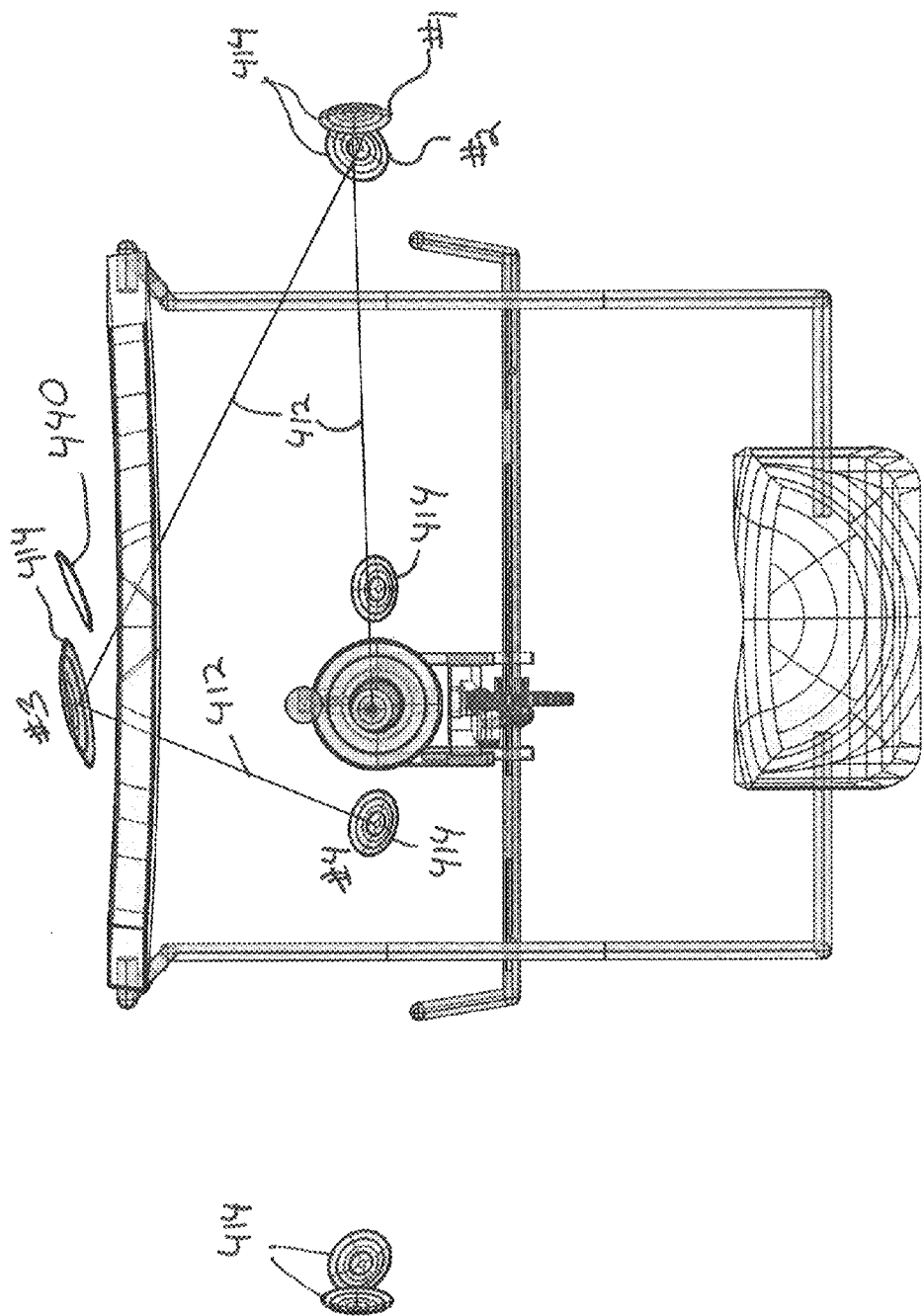
FIG. 20 is a top plan view of the alternative embodiment in FIG. 19. In this illustration, mirrors 1-4 for the left eye are labeled.
Figure 21:
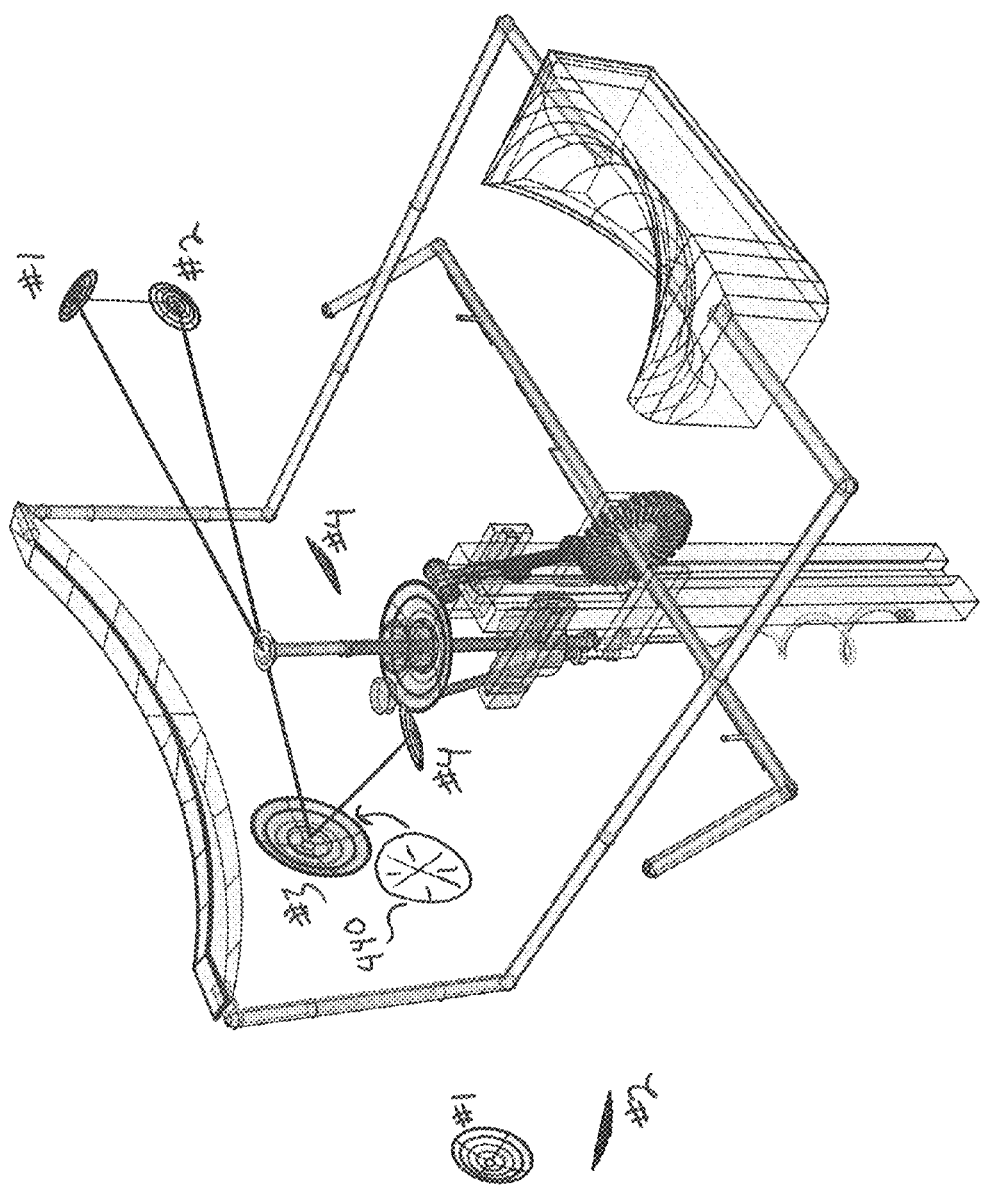
FIG. 21 is a perspective view of the alternative embodiment in FIG. 20. In this illustration, the line-of-sight for mirrors 1-4 can be seen.

In a first embodiment, a mirror system 410 is utilized for the display system to align the eye with the lens manipulator, as well as to create a overlaid image illusion or ultra-parallax image. With this embodiment, the viewing mechanism 405 is two or more mirrors that can be aligned to provide a line-of-sight 412 that allows the viewing or second eye of a user to see the action of the lens manipulator on the opposite or first eye. FIGS. 19, 20, and 21 illustrate one embodiment utilizing multiple mirrors to align the eye with the lens manipulator, where at least one of the mirrors is the viewing mechanism seen by the second eye. The type of mirrors utilized with this embodiment can be flat or can have a concavity or other shape that is conducive to reflecting the images therein.

FIG. 19 shows an embodiment that uses a series of concave mirrors 414 to direct an image to the left eye side of the lens manipulator 230. The line-of-sight 412 between each pair of mirrors can be aligned so that the final image is seen in the viewing mechanism 405, which can be a side mirror 415 directed towards the left eye, so a user looking into one mirror sees a view, such as, for example, an orthogonal view, of the process as reflected by another mirror. FIGS. 20 and 21 illustrate how a first mirror in the series 414, indicated by #1, reflects the lens manipulator approaching the right eye. The angle of mirror #1 directs the reflection to mirror #2 in the series, also indicated in FIGS. 20 and 21. Mirror #2 in turn reflects the image to mirror #3, which then reflects the image to the side mirror 415 to be directly visible to the left eye.

A similar but opposite mirror system can be configured for the right eye to see the left eye. Alternatively, the mirror system can be adjustable so that the mirrors can be rotated, manually or by an automatic system, to operate in the opposite directions. FIGS. 20 and 21 illustrate additional mirrors on the opposite side of mirrors #1 and #2. With this embodiment, readjusting mirror #3 will reflect an image to the right eye of the lens manipulator. The location of the mirrors can vary, as well as the number of mirrors utilized. It is within the skill of a person trained in the art to determine the number and location of mirrors, as well as their angle of reflection or concavity. Such variations are within the scope of this invention.

In a second embodiment, a digital imagery system 420 is utilized to provide the second image, which can be mentally combined with the first image, so that the dual images are perceived as overlaid independent images. This embodiment utilizes at least one, optionally two, viewing mechanisms, which can be electronic display screens 430 that are operably connected to at least one, optionally two, video cameras 425. For the following description, reference will be made to FIGS. 8, 10, 12, 14, and 16.

With the electronic imagery system 420, a motion-capture apparatus 425 can be directed towards about the side of the face of a user engaged with a CLIARA, so as with the mirror system, to provide a view, such as an orthogonal or other ultra-parallax view, to the line-of-vision of the second eye viewing the image. Motion-capture apparatuses are well-known to those with skill in the art and can include, but are not limited to, video cameras, cell phone cameras, single image cameras, and other image-capturing devices. FIGS. 10, 12, and 14 illustrate embodiments that use small, digital video cameras supported on stalks 432 and directed towards the face. Any of a variety of other types of digital video cameras can be used. In a specific embodiment, a motion-capture apparatus 425 can be aimed towards the side of the face so that the line-of-sight of the camera is generally orthogonal or perpendicular to the lens manipulator, specifically, perpendicular to the tube 234 and the cup 232, as it rises from the lens sink, which provides a line-of-sight to the motion-capturing apparatus that is orthogonal to the line-of-vision of the eyes when one is emplaced over the cup. Still more specifically, the camera 425 can be positioned so that it can capture both an image of a first eye from the side, or, for example, orthogonal to the line-of-vision of the first eye, and the lens manipulator and cup as they approach the first eye. FIGS. 10, 12, and 14 illustrate embodiments of a CLIARA that incorporates two cameras positioned so as to be on each side of the face of a user when engaged with a CLIARA. Each camera can be positioned on opposite sides of the CLIARA and so that the line-of-sight of each one is, for example, substantially perpendicular to the lens manipulator and so that each one can capture a profile image of one eye. FIGS. 12 and 14 illustrate embodiments with motion-capture apparatus, such as, for example, cameras, on the left side 40 and the right side 45 of a CLIARA. Each camera can be positioned so that its line of sight will capture a profile of an eye on the respective side of the CLIARA; the left side camera will obtain a profile image of the left eye and the right side camera will obtain a profile image of the right eye.

Thus, the user viewing the display screen 430 can see an orthogonal view of the process. As discussed above, the image presented to the second eye does not necessarily have to be orthogonal to the line of sight of the first eye. The image can be taken by the motion-capturing apparatus from any of a variety of angles that will provide a user with an adequate and/or beneficial view of the process that can be mentally overlaid with the image seen by the first eye, or by the eye presented over the lens manipulator.

In order to create a dual image to be combined and overlaid in the mind of a user, the image obtained by a video camera or other motion-capturing device can be directed towards whichever eye is not emplaced over the lens sink or, in other words, towards the eye that is not going to be approached by the lens manipulator 230. The typical device utilized to display video images is an electronic display screen 430. Electronic display screens capable of displaying video images can include, but are not limited to, liquid-crystal display (LCD), light-emitting diode (LED), and plasma screens, which are common today. However, it is within the skill of a person trained in the art to determine any of a variety of electronic display screens that could be used with the embodiments of the subject invention. Such variations, which provide the same features in substantially the same way with substantially the same result, are within the scope of this invention.

In one embodiment, at least one motion-capture apparatus has an operable communication with an electronic display screen. Such operable communication can be by direct electronic connection, such as with wires, cords, or it can be any type of remote or wireless connection. In a further embodiment, the at least one electronic display screen can be viewed with the eye that is not emplaced over the lens sink or that eye not being approached by the lens manipulator. In a similar fashion to a side-mirror embodiment, the motion-capture apparatus 425 will display on the electronic display screen 430 the motion an orthogonal view of the lens manipulator from the side as it approaches the eye. At the same time, the eye over the lens sink will see the lens manipulator approaching from different directions. Both of these images can be combined in the mind of the user into a single image of the lens manipulator approaching the eye from a sideways direction. The user can then watch the entire process of insertion or removal of a contact lens.

It is also possible for an electronic display screen 430 to be located in a position that is not directly visible to one or both eyes. With this arrangement, a secondary viewing device 450 can direct the image on the electronic display screen to the eye or to a location visible by one or both eyes. In one embodiment, a secondary viewing device comprises a prism. In a more specific embodiment, a secondary device comprises a reflective prism of any appropriate angle or reflectivity. Prisms are commonly used as visual aids and it is within the skill of a person trained in the art to determine any of a variety that would be appropriate for the subject invention. A prism may also be moveable or adjustable to accommodate individual users.

FIGS. 17 and 18 illustrate one embodiment having an electronic display screen placed perpendicularly to a lens sink, such that it is not viewable while a user has their head engaged with the CLIARA. A right angle prism can be placed on the CLIARA in a location, as demonstrated in FIG. 18, where the image on the electronic display screen is directed to a first surface of the prism and reflected onto a second surface of the prism. The second surface of the prism can be viewable by a user so that they see, indirectly, the image displayed on the electronic display screen. More than one prism, or more than one type of prism, can be used with the embodiments of the subject invention.

Understandably, when the display system or secondary viewing device is being used to install contact lenses, the person can have impaired vision at the outset of the process. This can make it difficult to see or focus on the digital viewing system or the secondary viewing apparatus. To accommodate such impairment, the components of a display system or the secondary viewing device can be adjustable so they can be moved to a position that a user can see. For example, the stalks that support one or more electronic display screens can be movable or adjustable so that the screens can be optimally positioned for use. Likewise, a secondary viewing device can be mounted to a CLIARA with devices or by techniques that would allow adjustability. A variety of devices and techniques can be used to provide adjustability to the display system and a secondary viewing device. Such variations are within the scope of this invention.

The embodiments of a CLIARA described herein can be arranged for single-eye use or double-eye use. FIGS. 3, 7, 8, 9, 12, and 14, for example, show embodiments having a single lens conveyor system 200, among other features. These arrangements require a user to move their head to a different position in order to align each eye with the lens manipulator 230. However, it is possible for a CLIARA to be configured with dual lens conveyor systems, an example of which is shown in FIGS. 17 and 18. This configuration would overcome the need for a user to move their head into a different position to engage each eye with a lens manipulator. Ideally, the lens conveyor system would be variously adjustable, so that the different components can be aligned to the features of a particular user. Once aligned, a user would not have to move their head to an entirely different position. Rather, they could place their head in, on, or against one or more props 290 and, if available, use one or more visual guides 216 to place each eye in the correct direction. In one embodiment, separate handles 280 can be used so that each lens conveyor system can be operated separately. In an alternative embodiment, a single handle can be used to raise each lens conveyor system at the same time. In yet another alternative embodiment, a single handle can be used to raise each lens conveyor system at different rates or at different times, such that a first eye can be engaged with a cup 232 on a first lens conveyor system and by continuing to turn the handle the second eye can be engaged with the cup on the second lens conveyor system. FIG. 17 shows an example of this embodiment with the lens manipulators in a fully down or "starting" position. To demonstrate the position of other possible components, the second support tower 250 has been removed, but the lens conveyor components left in place. FIG. 18 shows an example of dual lens conveyor systems with their lens manipulators completely raised and the second support tower indicated.

A fully hands-free system could include components for cleaning and storing contact lenses after being removed from a user with a CLIARA. Such a system could be incorporated with the lens conveyor system. Various types of fluids, such as cleaning, disinfecting, and storing fluids and more specific fluids, like protein-dissolving or saline solutions, are typically employed with the use of contacts. There are also sonicators and ultra-violet (UV) light devices that can be used to clean contact lens. A hands-free system could provide a storage container into which any desired fluid could be introduced. Various inserts or attachments that provide sonic or UV cleaning could also be used with a hands-free system.

In one embodiment, a storage well could be provided for one or both contact lenses. A storage well could be a separate container into which the contact can be deposited. Alternatively, a lens sink could be modified as a storage well.

In a further embodiment, a cap can be included on the storage well. A cap can have an inlet at the top or side for a fluid insertion hose fitting. An additional insert can be included for a UV lamp. The fluid insertion inlet could also be used for insertion of a UV lamp.

Maintaining the proper positioning of a contact lens in the storage well can be helpful. In one embodiment, a convex circular lattice, such as a colander-type configuration, that can be secured to the inside of the cap, so as to be situated above the lens when placed on the storage well, can be used to prevent a lens from moving out of position in the storage well.

An additional concave circular lattice can be positioned within a storage well for receiving and supporting a contact lens in the well. The concave circular lattice, located below the lens in a storage well, can also have a hole through the center to accommodate a lens manipulator 230. The lens manipulator can be positioned within the central hole. The cup 232 of the lens manipulator 232 can further fit into a depression at the distal end of the storage well interior. When the lens manipulator is fully withdrawn or in a fully distal position, the cup can be seated within the depression and operate to create a liquid-proof seal by contact with the storage well around the central hole. As the lens manipulator ascends towards the eye, it will pass through the central hole and contact the convex side of the lens and raise it towards the eye.

Non-fluid based cleaning techniques and devices can also be incorporated with a storage well. In one embodiment, the storage well, or a platform or support therefor, can have a physical connection, such as, for example, through a port, that accepts an ultrasonic transducer. The storage well can also have an additional vacuum hose fitting in the bottom or side. A fluid insertion hose can be attached to a manifold that, through the use of valves, can be used to control which of any of a variety of fluids is pumped into the storage well. Fluids pumped through the port can be vacuumed out either through a tubed rod 202, detailed above, a lens manipulator, or through an additional vacuum port, such as in the bottom or side of the storage well. The cap and storage well can be flushed and air dried through the use of forced air through the fluid insertion hose. In a fully automated version, the fluid pumps and vacuum can be controlled by a microprocessor.

The scope of the invention is not limited by the specific examples and suggested procedures and uses related herein since modifications can be made within such scope from the information provided by this specification to those skilled in the art.

All patents, patent applications, provisional applications, and other publications referred to or cited herein are incorporated by reference in their entirety, including all figures and tables, to the extent they are not inconsistent with the explicit teachings of this specification. Additionally, the entire contents of the references cited within the references cited herein are also entirely incorporated by reference.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. Further, when a particular feature, structure, or characteristic is described in connection with any embodiment, it is within the purview of one skilled in the art to affect such feature, structure, or characteristic in connection with other ones of the embodiments.

The invention has been described herein in considerable detail, in order to comply with the Patent Statutes and to provide those skilled in the art with information needed to apply the novel principles, and to construct and use such specialized components as are required. However, the invention can be carried out by specifically different equipment and devices, and that various modifications, both as to equipment details and operating procedures can be effected without departing from the scope of the invention itself. Further, although the present invention has been described with reference to specific details of certain embodiments thereof and by examples disclosed herein, it is not intended that such details should be regarded as limitations upon the scope of the invention except as and to the extent that they are included in the accompanying claims.

I claim:

1. A contact lens manipulating device comprising:
   a lens conveyor system comprising;
   a rod having a distal end and a proximal end, a lens manipulator having a distal end, a proximal end with a cup having an interior adapted to receive a contact lens, and a channel between the distal end and the proximal end that opens onto the distal end, wherein the distal end of the channel is positioned over the proximal end of the rod, a lens sink having an interior for receiving the cup and a port through which the rod reciprocates; and an actuator mechanism operably attached to the rod, where the actuator mechanism controls movement of the rod, thereby controlling movement of the lens manipulator thereon.

2. The device, according to claim 1, further comprising: a rod sleeve through which the rod is disposed so that the proximal end of the rod extends from a proximal end of the rod sleeve and where the rod sleeve is operably connected to the actuator mechanism, such that the actuator mechanism moves the rod sleeve with the rod therein through the port in the lens sink.

3. The device, according to claim 2, further comprising a compression element between the rod sleeve and the lens manipulator.

4. The device, according to claim 1, further comprising a pore in the cup that communicates the interior of the cup with the channel in the distal end of the lens manipulator.

5. The device, according to claim 4, wherein the rod transmits light to the pore in the cup.

6. The device, according to claim 5, wherein the cup comprises a pliable or deformable material.

7. The device, according to claim 6, wherein soft and hard contact lenses are manipulable with the cup.

8. The device, according to claim 6, wherein the rod is tubular, such that the tubular rod leads into the channel in the lens manipulator.

9. The device, according to claim 8, wherein the rod is attached to a fiber optic cable that provides a light source to the rod for transmission to the pore in the cup.

10. The device, according to claim 8, further comprising a pump operably attached to the tubular rod, where the pump creates a suction force in the cup.

11. The device, according to claim 4, further comprising a channel volume in the channel, between the proximal end of the rod and the pore in the cup, where the channel volume determines an amount of suction applied to a contact lens received in the interior of the cup.

12. The device, according to claim 11, wherein the lens manipulator is removable from the rod.

13. The device according to claim 12, further comprising:
a controller operably connected to the rod sleeve; and
an actuator apparatus having a proximal end operably connected to the controller and a distal end operably connected to the rod;
whereby activation of the controller causes the distal end of the actuator apparatus to push the rod distally so as to at least partially disengage the proximal end of the rod from the channel of the lens manipulator, thus releasing the suction force applied to the contact lens.

14. The device, according to claim 4, further comprising a pump operably attached to the channel, where the pump creates a suction force in the cup.

15. The device, according to claim 1, wherein the actuator mechanism is manually controlled.

16. The device, according to claim 1, wherein the actuator mechanism is automated.

17. The device, according to claim 1, wherein the interior of the lens sink is at least partially complementary to a shape of a contact lens.

18. The device, according to claim 17, further comprising:
one or more drain holes in the lens sink; and
an overflow cup distal to the lens sink having a storage space for receiving a fluid from the drain holes in the lens sink.

* * * * *